(12) United States Patent
Elliott Brown et al.

(10) Patent No.: US 10,136,608 B2
(45) Date of Patent: *Nov. 27, 2018

(54) TOBACCO HAVING REDUCED AMOUNTS OF AMINO ACIDS AND METHODS FOR PRODUCING SUCH LINES

(71) Applicant: Reynolds Technologies, Inc., Winston-Salem, NC (US)

(72) Inventors: Patsy Elizabeth Elliott Brown, Winston-Salem, NC (US); Darlene Madeline Lawson, Kernersville, NC (US); Serban C. Moldoveanu, Winston-Salem, NC (US)

(73) Assignee: Reynolds Technologies, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/350,515

(22) Filed: Nov. 14, 2016

(65) Prior Publication Data
US 2017/0181398 A1    Jun. 29, 2017

Related U.S. Application Data

(63) Continuation of application No. 14/255,544, filed on Apr. 17, 2014, now Pat. No. 9,491,968, which is a continuation of application No. 13/238,181, filed on Sep. 21, 2011, now Pat. No. 8,716,571.

(51) Int. Cl.
| | |
|---|---|
| *A01H 5/12* | (2018.01) |
| *A01H 5/00* | (2018.01) |
| *A01H 1/06* | (2006.01) |
| *A24B 15/10* | (2006.01) |
| *A24B 15/20* | (2006.01) |

(52) U.S. Cl.
CPC .............. *A01H 5/12* (2013.01); *A01H 1/06* (2013.01); *A01H 5/00* (2013.01); *A24B 15/10* (2013.01); *A24B 15/20* (2013.01)

(58) Field of Classification Search
CPC ................................................ A01H 5/00
See application file for complete search history.

(56) References Cited

U.S. PATENT DOCUMENTS

| | | | |
|---|---|---|---|
| 4,407,307 A | 10/1983 | Gaisch et al. |
| 4,537,204 A | 8/1985 | Gaisch et al. |
| 5,539,093 A | 7/1996 | Fitzmaurice et al. |
| 5,668,295 A | 9/1997 | Wahab et al. |
| 5,670,349 A | 9/1997 | Cramer et al. |
| 5,705,624 A | 1/1998 | Fitzmaurice et al. |
| 5,741,898 A | 4/1998 | Hanley et al. |
| 5,837,876 A | 11/1998 | Conkling et al. |
| 6,030,462 A | 2/2000 | Shu et al. |
| 6,730,832 B1 | 5/2004 | Dominguez et al. |
| 7,173,170 B2 | 2/2007 | Liu et al. |
| 7,825,305 B2 | 11/2010 | Dominguez et al. |
| 8,716,571 B2* | 5/2014 | Elliott ...................... A01H 1/06 131/374 |
| 9,137,958 B2 | 9/2015 | Elliott et al. |
| 9,491,968 B2* | 11/2016 | Elliott Brown .......... A01H 1/06 |
| 2006/0185686 A1 | 8/2006 | Lawrence, Jr. |
| 2007/0006888 A1 | 1/2007 | Hicks et al. |
| 2009/0123626 A1 | 5/2009 | Rommens et al. |
| 2010/0136169 A1 | 6/2010 | Van Der Laan et al. |
| 2011/0023178 A1 | 1/2011 | Dominguez et al. |
| 2011/0048434 A1 | 3/2011 | Chen et al. |
| 2011/0174323 A1 | 7/2011 | Coleman, III et al. |
| 2013/0199553 A1 | 8/2013 | Elliott et al. |

FOREIGN PATENT DOCUMENTS

| | | |
|---|---|---|
| CN | 101663395 | 3/2010 |
| WO | 1998/056923 | 12/1998 |
| WO | 2011/0116144 A2 | 3/2001 |
| WO | 2002/100199 | 12/2002 |
| WO | 2009/074325 A1 | 6/2009 |
| WO | 2012/028309 | 3/2012 |
| WO | 2012/041913 | 4/2012 |
| WO | 2013/038202 A2 | 3/2013 |

OTHER PUBLICATIONS

Lea et al. (Plant Physiology (2006) 140: 1085-1094.*
Lea et al. (Annals App. Biol. (2007) 150: pp. 1-26.*
Matt et al. (Plant J. (2002) 30: 663-677.*
Zyzak et al., J. Agric. Food Chem. (2003) 51: pp. 4782-4787.*
Olesen et al., Int. J. Cancer (2008) 122: pp. 2094-2100.*
Kaye et al., Plant Molec. Biol. (1997) 33: pp. 953-964.*
Rousselin et al., Theor. Appl. Genet. (1992) 85: pp. 213-221.*
Rommens et al., J. Agric. Food Chem. (2007) 55: pp. 4281-4288.*
Bourgin et al., Genetics (1985) 109: pp. 393-407.*
Lea et al, Plant Physiology; 2006, vol. 140: pp. 1085-1094.*
Lea et al., Annals App. Biol.; 2007, vol. 150: pp. 1-26.*
U.S. Appl. No. 11/584,378, Office Action dated Oct. 21, 2009.
U.S. Appl. No. 11/584,378, Office Action dated Mar. 5, 2009.
U.S. Appl. No. 11/584,378, Office Action dated Jul. 22, 2008.
U.S. Appl. No. 11/584,378, Office Action dated Dec. 11, 2007.
U.S. Appl. No. 13/238,181, Non Final Office Action dated Jun. 28, 2013.
U.S. Appl. No. 12/804,617, Office Action dated Mar. 14, 2014.
U.S. Appl. No. 12/804,617, Office Action dated Oct. 9, 2013.
U.S. Appl. No. 12/804,617, Office Action dated Apr. 21, 2011.
U.S. Appl. No. 13/368,797, Office action dated Oct. 8, 2014.
U.S. Appl. No. 13/368,797, Office action dated Feb. 5, 2015.
U.S. Appl. No. 14/255,544, Non-Final Office Action dated Nov. 25, 2015.
U.S. Appl. No. 14/255,544, Final Office Action dated May 2, 2016.

(Continued)

*Primary Examiner* — Russell Kallis
(74) *Attorney, Agent, or Firm* — Kilpatrick Townsend & Stockton LLP

(57) ABSTRACT

The present invention discloses genetically modified tobacco plants, and tobacco products derived from such plants, comprising a decrease in at least one amino acid such that upon heating and/or burning, the tobacco plant or a portion thereof generates reduced levels of a compound derived from the at least one amino acid as compared to an unmodified parent tobacco plant or a portion thereof. In an embodiment, the tobacco generates reduced levels of acrylamide and/or acrylonitrile upon heating and/or burning of the tobacco as compared to an unmodified parent tobacco line. These plants are useful for improving tobacco products.

20 Claims, 2 Drawing Sheets

(56) References Cited

OTHER PUBLICATIONS

Adamu, et al., "Residual metal concentrations in soils and leaf accumulations in tobacco a decade following farmland application of municipal sludge", Environ Pollut., 56(2):113-26, 1989.
Bourgin, J. et al., "Valine-Resistance, A Potential Marker in Plant Cell Genetics", Distinction between Two Types of Valine-Resistant Tobacco Mutants Isolated from Protoplast-Derived Cells. Genetics, vol. 109, pp. 393-407, Feb. 1985.
Bright, S. W. et al., "Two Genes for Threonine Accumulation in Barley Seeds", Nature, 299:278-279,1982, 1982.
Bright, S. W. et al., "Threonine Accumulation in the Seeds of a Barley Mutant with an Altered Kinase", Biochem. Genet., 20:229-243, 1982.
Broun, P. et al., (2001), "Progress in Plant Metabolic Engineering", PNAS, 98:8925-8927, 2001.
Cattoir-Reynaerts, A. et al, "Selection and Characterization of Carrot Embryoid Cultures Resistant to Inhibition by Lysine Plus Threonine", Biochem. Physiol. Pflanzen, 178: 81-90,1983.
Chen, J. et al., "Comparison of volatile generation in serine/threonine/glutamine-ribose/glucose/fructose model system", J. Agric. Food Chem., 47: 643-647, 1999.
State Intellectual Property Office of the Peoples Republic of China Application No. 201280057049.X, First Office Action dated Jun. 3, 2015.
State Intellectual Property Office of the Peoples Republic of China Application No. 201280057049.X, Office Action dated Feb. 24, 2016.
State Intellectual Property Office of the Peoples Republic of China Application No. 201280057049.X, Office Action dated Nov. 7, 2016.
State Intellectual Property Office of the Peoples Republic of China Application No. 201280057049.X, Office Action dated May 19, 2017.
State Intellectual Property Office of the Peoples Republic of China Application No. 201380016376.5, Office Action dated Oct. 9, 2015.
State Intellectual Property Office of the Peoples Republic of China Application No. 201380016376.5, Office Action dated Aug. 24, 2016.
Currin, R. et al., "Registration of Clemson PD4 Flue-Cured Tobacco", Copr Sci., 21:988, 1981.
Devi, S. et al., "Isolation of aluminum-tolerant cell lines of tobacco in a simple calcium medium and their responses to aluminum", Physiol. Plant, 112(3):397-402, 2001.
Diedrick et al., (1990), "Tissue Culture Isolation of a Second Mutant Locus for Increased Threonine Accumulation in Maize", Theor. Appl. Genet., 79:209-215, 1990.
Dotson et al, "Lysine-Insensitive Aspartate Kinase in Two Threonine-Overproducing Mutants of Maize", Planta, 182: 546-552, 1990.
Ellstrand, (2001), "When transgenes wander, should we worry?", Plant Physiol., 125: 1543-1545, 2001.
European Patent Application No. 12834296.1, Extended Search Report dated Dec. 12, 2014.
European Patent Application No. 12834296.1, Office Action dated Sep. 24, 2015.
European Patent Application No. 12834296.1, Office Action dated Aug. 4, 2016.
European Patent Application No. 12834296.1, Office Action dated Mar. 23, 2017.
European Patent Application No. 13705873.1, Office Action dated Oct. 2, 2015.
European Patent Application No. 13705873.1, Office Action dated Oct. 25, 2016.
Falco, S. et al., (1995), "Transgenic canola and soybean seeds with increased lysine", Biotechnology 13: 577-582, 1995.
Falco, S. et al., "Using bacterial genes to engineer plants with increased seed lysine", SIM News 47: 53-57, 1997.
FEHR, Mutation Breeding, in Applied Plant Breeding, Chapter 6, pp. 6-1 to 6-30, $2^{nd}$ Edition Iowa State University, Ames, IA, 1983.

Frankard,V. et al., "Two Feedback-Insensitive Enzymes of the Aspartate Pathway in Nicotiana sylvestris", Plant Physiol., 99:1285-1293, 1992.
Frankard,V. et al., "High Threonine Producer Mutant of Nicotiana sylvestris (spegg. And comes)", Theor. Appl. Genet., 82:273-282., 1991.
Galili, G., "Regulation of Lysine and Threonine Synthesis", The Plant Cell, 7: 899-906, 1995.
Galili,il, V. et al., "Enhancing the Content of Essential Amino Acids Lysine and Threonine in Plants, In: Plant Amino Acids in Biochemistry and Biotechnology", B.K. Singh, ed., Marcel Dekker, New York, pp. 487-507,1999.
Haughn, G. et al., "Selection for Herbicide Resistance at the Whole Plant Level, in: Biotechnology in Agricultural Chemistry", H. M. Lebaron (ed.), American Chemical Society, Washington, D.C., pp. 98-107, 1987.
Heremans, B. et al., "Threonine Accumulation in a Mutant of *Arabidopsis thaliana* (L.) Heynh, with an Altered Aspartate Kinase", J. Plant Physiol., 146: 249-257, 1995.
Hibberd, K. A. et al, "Selection and Characterization of a Feedback-Insensitive Tissue Culture of Maize", Planta, 148: 183-187, 1980.
Howden, R., "Cadmiun-sensitive mutants of a *Arabidopsis thaliana*", Plant Physiol., 100(1):100-107, 1992.
IKUSHUGAKU, New edition, Breeding of Plants, Fifth Edition, Apr. 1, 1997, p. 53.
Imsande, J., "Selection of Soybean Mutants with Increased Concentrations of Seed Methionine and Cysteine", Crop Sci., 41:510-515, 2001.
Japanese Patent Office Application No. 2014-531959, Office Action dated Jul. 26, 2016.
Karchi, H. et al., "Seed-specific expression of a bacterial desensitized aspartate kinase increases the production of seed threonine and methionine in transgenic tobacco", Plant J., 3: 721-727, 1993.
Kaye, C. et al., "Constitutive non-inducible expression of the *Arabidopsis thaliana* Nia 2 gene in two nitrate reductase mutants of Nicotiana Plumbaginifolia", Plant Molecular Biology, vol. 33, No. 6, pp. 953-964, Apr. 1997.
Lea, P. et al., "Asparagine in Plants", Annals of Applied Biology, vol. 150, Dec. 31, 2007, pp. 1-26, 2006.
Lea, P. et al., The Biosynthesis of Amino Acids in Plant, In: Chemistry and Biochemistry of the Amino Acids, G.C. Barrett, ed.. Chapman & Hill , London, pp. 197-226, 1985.
Lea, P. et al., "Posttranslational Regulation of Nitrate Reductase Strongly Affects the Levels of Free Amino Acids and Nitrate, whereas Transcriptional Regulation Has Only Minor Influence", Plant Physiology, 140:1085-1094, 2006.
Lee et al., "Functional expression of a bacterial heavy metal transporter in *Arabidopsis* enhances resistance to and decreases uptake of heavy metals", Plant Physiol., 133(2):589-96, Epub 2003.
Lu, G. et. al., "Generation of Flavor Compounds by the Reaction of 2-Deoxyglucose with Selected Amino Acids", J. Agric. Food Chem., 45: 233-236, 1997.
Lugon-Moulin, et al., "Cadmium concentration in tobacco (*Nicotiana tabacum* L.) from different countries and its relationship with other elements", Chemosphere. 63(7):1074-86. Epub 2005.
Lugon-Moulin, et al., "Cadmium content of phosphate fertilizers used for tobacco production", Agron. Sustain. Dev, 26:151-156, 2006.
Malmberg, R. et al., Chapter 2; Production and Analysis of Plant Mutants, Emphasizing *Arabidopsis thaliana*, in: Methods in Plant Molecular Biology and Biotechnology, B. R. Glick and J. E. Thompson, (eds.), CRC press, 1993.
Matt, P. et al., "Decreased Rubisco Activity Leads to Dramatic Changes of Nitrate Metabolism, Amino Acid Metabolism and the Levels of Phenylpropanoids and Nicotine in Tobacco Antisense RBCS Transformants", Plant J., 30:663-677, 2002.
Matthews, B. F., "Lysine, Threonine and Methionine Biosynthesis", in: Plant Amino Acids Biochemistry and Biotechnology, B. K. Singh, (ed.), Marcel Dekker, Inc., New York, pp. 205-225, 1999.
Moldoveanu, et al., "Acrylamide analysis in tobacco, alternative tobacco products, and cigarette smoke", J. Chromatogr. Sci., 49: 234-242, 2011.

(56) References Cited

OTHER PUBLICATIONS

Olesen, P. et al., "Acrylamide Exposure and Incidence of Breast Cancer among Postmenopausal Women in the Danish Diet", Cancer and Health Study, Int. J. Cancer, 122, 2008, 2094-2100, 2008.

Peng, et al., "Derivative Alleles of the *Arabidopsis* Gibberellin-Insensitive (gai) Mutation Confer a Wild-Type Phenotype", The Plant Cell, 5: 351-360, 1993.

Patent Cooperation Treaty, International Search Report and Written Opinion, International Application No. PCT/US2013/024730, dated May 6, 2013.

Patent Cooperation Treaty, International Search Report and Written Opinion, International Application No. PCT/US12/56303, dated Nov. 23, 2012.

Rommens, C. et al., "Intragenic Crop Improvements: Combining the Benefits of Traditional Breeding and Genetic Engineering", J. Agric. Food Chem., 55:4281-4288, 2007.

Rousselin, P. et al., "Characterization of Three Hormone Mutants of Nicotiana Plumbaginifolia: Evidence for a Common ABA Deficiency", Theor. Appl. Genet., 85:213-221, 1992.

"Screening for an *Arbbidopsis* Mutant with Enhanced Tolerance to Cadmium Toxicity, CAO Shuqing, Acta Scientiae Circumstantiae", vol. 26 No. 2, pp. 318-322, 2006.

Shauli, O. et al., "Threonine Overproduction in Transgenic Tobacco Plants Expressing a Mutant Desensitized Aspartate Kinase of *Escherichia coli*.", Plant Physiol, 100:1157-1163,1992.

Van Harten, A. M., "Mutation Breeding, Theory and Practical Applications", pp. 1-63, Cambridge Univ. Press, New York, N.Y., 1998.

Wagner, et al., "Variation in cadmium accumulation potential and tissue distribution of cadmium in tobacco," Plant Physiol., 82(1):274-9,1986.

Williams, J. et al., "Changes in Amino Acid Content of Flue-Cured Tobacco During Natural Aging", Tobacco Science, 128:243-247,1968.

Zyzak, D. et al., "Acrylamide Formation Mechanism in Heated Foods", Journal of Agricultural Food Chemicals, 51: pp. 4782-4787, Jun. 2003.

Japanese Patent Office Application No. 2014-531959, Examiner's Decision of Rejection dated Jun. 13, 2017, 6 pages.

SHIN-PAN, Shokubutsu-Ikushugaku, (New Edition, Breeding of Plants), Fifth Edition, Apr. 1, 1997, p. 53.

European Patent Office Application No. 12834296.1, Communication Pursuant to Article 94(3) EPC dated Nov. 13, 2017, 3 pages.

\* cited by examiner

TOBACCO HAVING REDUCED AMOUNTS OF AMINO ACIDS AND METHODS FOR PRODUCING SUCH LINES

RELATED APPLICATIONS

The present application is a continuation application of pending U.S. patent application Ser. No. 14/255,544, filed Apr. 17, 2014, entitled "Tobacco Having Reduced Amounts of Amino Acids and Methods For Producing Such Lines and U.S. patent application Ser. No. 13/238,181, filed Sep. 21, 2011, entitled "Tobacco Having Reduced Amounts of Amino Acids and Methods For Producing Such Lines." The disclosure of U.S. patent application Ser. No. 14/255,544 and U.S. patent application Ser. No. 13/238,181 are incorporated by reference in their entirety herein.

FIELD OF THE INVENTION

The present invention relates to a method for producing plants with an altered phenotype, by selection of mutants at the M0 chimeric stage. Embodiments of the present invention provide tobacco plants having a lower than average level of at least one amino acid. These plants are useful for developing tobacco products that generate lower amounts of certain non-natural chemicals upon heating and/or burning.

BACKGROUND OF THE INVENTION

The biosynthesis of amino acids in plants is highly regulated (Lea et al., 1985, *The Biosynthesis of Amino Acids in Plant, In*: Chemistry and Biochemistry of the Amino Acids, G. C. Barrett, ed., Chapman & Hill, London, pp. 197-226). Due to the general desirability for essential amino acids in grains and other foods, several approaches have been developed to enhance the content of amino acids in plants (see e.g. G. Galili and B. A. Larkins, 1999, *Enhancing the Content of Essential Amino Acids Lysine and Threonine in Plants,* In: Plant Amino Acids in Biochemistry and Biotechnology, B. K. Singh, ed., Marcel Dekker, Inc., New York, pp. 487-507). Also, in tobacco, certain amino acids can be a major source for flavor and aroma production.

However, amino acids undergo the Maillard reaction and Stecker Degradations in tobacco and produce pyrazines and other nitrogen containing compounds, some of which may not be beneficial. The amino acid profile affects not only the yield, but also the type, of pyrazines formed (Lu, G., et. al., 1997, *J. Agric. Food Chem.,* 45: 233-236; J. Chen and C.-T. Ho, 1999, *J. Agric. Food Chem.,* 47: 643-647). Thus, although there has been a focus on increasing amino acid levels in tobacco, there may also be a need to produce tobacco plants, and tobacco products derived from such plants, having reduced amounts of certain amino acids. Certain amino acids may be associated with the production of potentially harmful chemicals upon heating and/or burning the tobacco. For example, tobacco smoke may include acrylamide, which has been characterized as a Group 2A carcinogen by the International Agency for Research on Cancer (IARC). Also, acrylonitrile is a IARC Group B1 carcinogen found in cigarette smoke.

Thus, there is a general need for methods that can provide plant lines comprising reduced biosynthesis of particular amino acids. The methods should be designed so that they can be used even for plant species such as tobacco that are large so as to require extensive facilities for breeding, and that have a complex genome and thus can require screening of a large number of mutation events to isolate the mutation of interest.

SUMMARY OF THE INVENTION

The invention provides methods of making plants having a decreased level of at least one endogenous amino acid. In certain aspects, the invention comprises tobacco plants, or tobacco lines derived from such plants, having a decreased level of at least one endogenous amino acid. In certain embodiments, the invention comprises tobacco products made from tobacco plants having a decreased level of at least one endogenous amino acid.

In one embodiment, the invention comprises a method for producing a modified tobacco plant comprising generating a tobacco plant having a reduced level of at least one endogenous amino acid, such that the tobacco plant or a portion thereof generates a reduced level of at least one compound derived from the at least one endogenous amino acid, as compared to an unmodified parent tobacco plant or a portion thereof from which the modified plant is derived.

Also, in certain embodiments, the invention may comprise a method for producing a modified tobacco plant comprising a reduced level of at least one endogenous amino acid as compared to an unmodified tobacco plant comprising the steps of: incubating at least one seed from the unmodified tobacco plant in a solution comprising a mutagen; washing the at least one seed free of the mutagen; exposing the at least one M0 tobacco seed to a selection agent; germinating the at least one seed and growing at least one M0 tobacco seedling in the presence of a selection agent; growing the at least one M0 tobacco seedling to generate at least one M0 tobacco plant comprising M1 tobacco seeds, wherein the M1 tobacco seeds from the M0 tobacco plant comprise at least one mutagenized M1 tobacco seed; and germinating the at least one mutagenized M1 tobacco seed to select for a modified M1 tobacco plant comprising a reduced level of at least one amino acid as compared to the unmodified tobacco plant from which the modified plant is derived.

In yet other embodiments, the invention may comprise a modified tobacco plant or a portion thereof comprising a decrease in the level of at least one endogenous amino acid as compared to an unmodified tobacco plant or portion thereof from which the plant is derived. In an embodiment, the tobacco plant or a portion thereof generates a reduced level of a compound derived from the at least one endogenous amino acid, as compared to an unmodified parent tobacco plant or a portion thereof. For example, in certain embodiments, the invention may comprise a modified tobacco plant or a portion thereof comprising a decrease in acrylamide levels and/or acrylonitrile levels upon heating and/or burning of the tobacco plant or portion thereof.

In yet other embodiments, the invention may comprise a tobacco product derived from a modified tobacco plant of the invention, the tobacco product comprising a modified tobacco having a reduced level of at least one endogenous amino acid as compared to an unmodified tobacco plant from which the modified tobacco plant is derived. In an embodiment, the tobacco product generates a reduced level of a compound derived from the at least one amino acid, as compared to a tobacco product comprising an unmodified parent tobacco plant or a portion thereof. For example, the invention may comprise a modified tobacco product having a reduced level of acrylamide and/or acrylonitrile upon heating and/or burning of the tobacco product as compared to an unmodified tobacco.

BRIEF DESCRIPTION OF THE DRAWINGS

Various features, aspects, and advantages of the present invention will become more apparent with reference to the following description, appended claims, and accompanying drawings.

DETAILED DESCRIPTION

Figure 1:
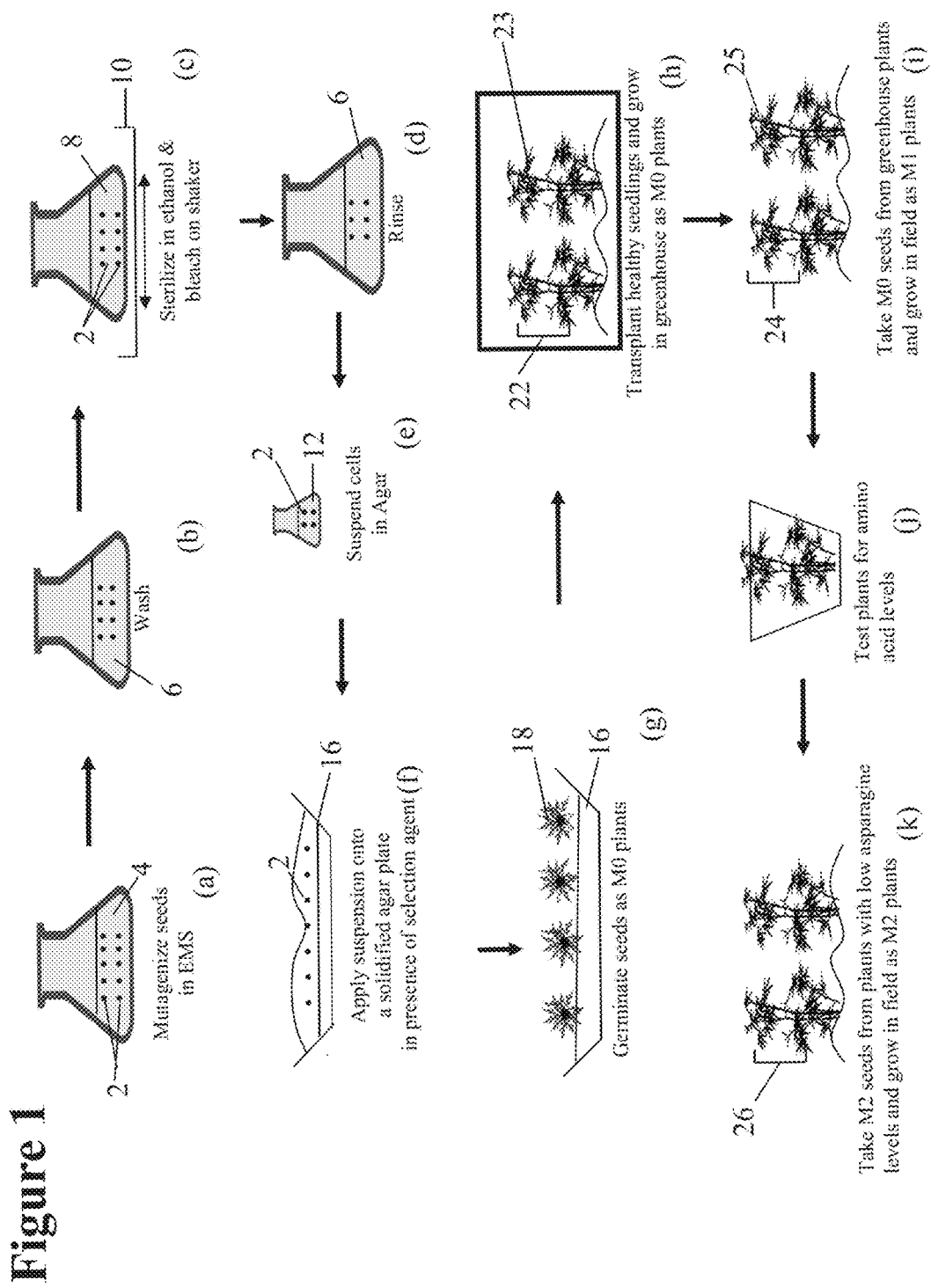
FIG. 1 is a schematic representation illustrating a method for generating tobacco lines with a reduced level of at least one amino acid according to one embodiment of the invention.

As used in this specification and the claims, the singular forms "a," "an," "at least one," and "the" include plural referents unless the context clearly dictates otherwise. Also the terms "seed(s)" and "seedling(s)" include single and plural referents. Reference to "dry weight percent" or "dry weight basis" refers to weight on the basis of dry ingredients (i.e., all ingredients except water).

The term "endogenous" refers to compounds (e.g., amino acids) that are generated by the plant as a result of normal biochemical reactions. These endogenous compounds do not include compounds that are added to the plant from an external source (e.g., compounds applied to the surface of the leaf and the like).

The term "non-natural" refers to compounds that are not naturally ingested and/or synthesized in the body of a plant or an animal, but that can be derived from endogenous compounds. In some cases, the non-natural compound may be a carcinogen. Or, the non-natural compound may have other potentially harmful or non-beneficial effects when ingested by some humans.

As defined herein, media may comprise compositions which are suited for maintenance or growth of biological tissue. Media may comprise water, buffered solutions, agar, or a growth medium, such as, but not limited to, the media described in the examples herein. Generally, any composition which is biologically compatible with the plant of interest may be suitable for use as a media or part of a media.

Also as defined herein, mutagenesis comprises a process that results in a modification of a DNA sequence. The term "mutagenesis" refers to the use of a mutagenic agent to induce genetic mutations within a population of individuals. A population to be mutagenized can comprise plants, parts of plants, or seeds. For mutagenized populations the dosage of the mutagenic chemical or radiation can be determined experimentally for each type of plant tissue such that a mutation frequency that is below a threshold level characterized by lethality or reproductive sterility is obtained. The number of M1 generation seed or the size of M1 plant populations resulting from the mutagenic treatments can be estimated based upon the expected frequency of mutations.

The types of mutations that may be induced in a gene include, for example, point mutations, deletions, insertions, duplications, and inversions. Mutagenesis may include transitions, transversions, base additions or deletions causing frameshifts, or crosslinking of nucleotides, as well as modification/substitution of bases such that binding of proteins to DNA (e.g. transcription factors) is altered. Also included are hybrids made from such mutants as well as interspecific and intraspecific crosses.

In addition to the methods described in detail herein, in some embodiments, mutagenesis may be induced by growing plant cells in tissue culture, which can result in the production of somaclonal variants. Alternatively, application of standard protoplast culture methodologies developed for production of hybrid plants using protoplast fusion is also useful for generating plants having variant gene expression. Accordingly, protoplasts may be generated from a first and a second plant having variant gene expression. Calli may be cultured from successful protoplast fusions and plants regenerated. Resulting progeny hybrid plants may be identified and selected for variant gene expression according to methods described herein and may be used in a breeding protocols described herein. Also included are methods comprising genetic engineering such as site-directed mutagenesis.

The plants included in the present invention also include plants (and/or tobacco lines derived from such plants) which may be genetically engineered using non-tobacco DNA at a locus distinct from the genes relating to production of the amino acid of interest (i.e., the amino acid for which decreased concentration in the tobacco is the end result). For example, plants which are genetically engineered to be resistant to pesticides and which are also modified by mutagenesis of tobacco genomic DNA by the techniques of the invention (e.g., at the asparaginase, asparagine synthetase or other amino acid biosynthesis loci to become low asparagine producers) are included in the present invention. In one embodiment, the plants of the present invention comprise plants having essentially the same antibiotic resistance profile as the unmodified plant parent line, such that the modified plants do not comprise a novel antibiotic resistance as compared to the unmodified parent line.

A mutagen is defined as a substance (or treatment) which can change (mutate) the DNA in a cell. Suitable mutagenic agents include, for example, chemical mutagens and ionizing radiation. Typical chemical mutagens include, but are not limited to, ethyl methanesulfonate (EMS), nitrous acid, 5-bromouracil, methyl-nitrosoguanidine, sodium azide, acridine orange, ethidium bromide and frameshift mutagens such as proflavin and the like. Mutations can also be generated by radiation, such as UV, X-rays, γ-rays, fast neutron irradiation, and the like. Mutagens also include genetic elements such as viral vectors, transponsons, and the like, which can facilitate the insertion of foreign DNA into the tobacco genome.

Generally, the first generation treated with a mutagen comprises the M0 (or $M_0$) generation. Subsequent generations are then described as M1 (or $M_1$) (i.e., one generation after the mutagenesis event), M2 (two generations after the mutagenesis event) and the like. Thus, as used herein, M0 refers to plant cells (and plants grown therefrom) exposed to a mutagenic agent, while M1 refers to seeds produced by self-pollinated M0 plants, and plants grown from such seeds. M2 is the progeny (seeds and plants) of self-pollinated M1 plants, M3 is the progeny of self-pollinated M2 plants, and M4 is the progeny of self-pollinated M3 plants. M5 is the progeny of self-pollinated M4 plants. Thus, the Mn+1 (or $M_{n+1}$) generation each the progeny of self-pollinated plants of the previous Mn (or $M_n$) generation.

As used herein, a "modified plant", or "modified tobacco plant" or "modified tobacco" includes plants, tobacco plants and tobacco that is genetically modified (i.e., mutated) so as to have a different genotype and phenotype than the unmodified plant (e.g., tobacco) from which the modified plant is derived.

As used herein, the "unmodified plant from which the modified plant is derived" refers to the parent plant line used to generate mutant plant lines. As used herein, the M0 generation would be the unmodified plant from which the modified M1 plant is derived.

As defined herein, the physical appearance of an organism comprises its phenotype, whereas the genetic composition of an organism comprises its genotype. Heterozygotes are defined as genomes which have different alleles (i.e., DNA sequences) at a locus of interest. For example, a heterozygous mutation would be a plant having a mutated sequence at only one allele. Thus, heterozygotes have two distinct alleles for a gene, each of which can be passed to the next generation. Homozygotes are defined as organisms having identical alleles at one or more loci. Thus, homozygotes carry the same alleles (e.g. two mutations or two normal sequences) at a locus of interest and, therefore, identical alleles will be passed to all progeny.

Thus, embodiments of the present invention provide methods of making tobacco plants (or tobacco lines derived from such plants) having a decreased level of at least one endogenous amino acid. In an embodiment, the invention comprises tobacco plants, or portions thereof, having a decreased level of at least one endogenous amino acid. In certain embodiments, the invention comprises tobacco products made from modified tobacco plants, or portions thereof, having a decreased level of at least one endogenous amino acid.

In certain embodiments of each of the methods, plants, plant lines, or tobacco products of the invention, the amino acid having decreased levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels is glutamic acid. Or, levels of other amino acids (e.g., aspartic acid, cysteine, glycine, selenocysteine, tyrosine, arginine, ornithine, taurine, isoleucine, leucine, lysine, methionine, phenylalanine, threonine, tryptophan, or valine) may be reduced.

It has been found that acrylamide may be generated upon heat-treatment and/or burning of tobacco (e.g., smoking) (see e.g., US Patent Publication No. 2011/0048434, the disclosure of which is incorporated by reference in its entirety herein). Also, acrylonitrile is a IARC Group B1 carcinogen found in cigarette smoke.

In certain embodiments, decreasing the asparagine levels in tobacco results in decreased levels of acrylamide and/or acrylonitrile and/or other non-natural compound formation in smoke derived from the tobacco (i.e., e.g., upon heating and/or burning a tobacco product comprising the tobacco). Also, in certain embodiments, decreasing the levels of at least one of alanine, asparagine, glutamic acid, glutamine, proline, histidine, lysine, phenylalanine and/or serine in tobacco results in decreased levels of acrylamide and/or acrylonitrile and/or other non-natural compound formation in smoke derived from the tobacco (i.e., e.g., upon heating and/or burning a tobacco product comprising the tobacco). Also, small amounts of acrylamide and/or acrylonitrile may be generated by heat curing tobacco. Thus, in certain embodiments, the methods and/or tobacco plants of the invention may be used to generate tobacco products having reduced acrylamide and/or acrylonitrile and/or other non-natural other chemicals that are produced from certain amino acids.

The present invention may be embodied in a variety of ways.

In one embodiment, the invention comprises a method for producing a modified tobacco plant comprising generating a tobacco plant comprising a reduced level of at least one endogenous amino acid as compared to an unmodified plant from which the modified plant is derived. In an embodiment, the tobacco plant or a portion thereof generates a reduced level of at least one compound derived from the at least one amino acid as compared to the unmodified parent tobacco plant or a portion thereof.

In an embodiment, the compound derived from the amino acid having reduced levels is a potential carcinogen. Or, the compound derived from the amino acid having reduced levels may be another type of compound which is potentially not beneficial to a consumer of the tobacco product. For example, in certain embodiments, upon heating and/or burning, the tobacco plant or a portion thereof generates reduced levels of acrylamide and/or acrylonitrile as compared to an unmodified parent tobacco plant or a portion thereof. Or, other potentially non-beneficial compounds may be reduced.

In an embodiment, the modified tobacco is made by the steps of incubating at least one tobacco seed from an unmodified tobacco plant in a solution comprising a mutagen; washing the at least one seed free of the mutagen; exposing the at least one seed to a selection agent; germinating the at least one seed and growing at least one M0 tobacco seedling in the presence of the selection agent; growing the at least one M0 tobacco seedling to generate at least one M0 tobacco plant comprising at least one mutagenized M1 tobacco seed; and germinating the at least one mutagenized M1 tobacco seed to select for at least one modified M1 tobacco plant comprising a reduced level of the at least one amino acid as compared to the unmodified tobacco plant.

A variety of amino acids may be targeted using the methods of the invention. In certain embodiments, the amino acid having reduced endogenous levels comprises at least one of asparagine or glutamic acid. In an embodiment, the modified tobacco plant comprises at least a 50% reduction in asparagine levels. Additionally or alternatively, the modified tobacco plant may comprise at least a 40% reduction in glutamic acid levels.

In an embodiment, the modified tobacco plant is the species *Nicotiana tabacum*.

The present invention may also comprise a method to make a modified tobacco plant having a reduced level of at least one endogenous amino acid as compared to an unmodified tobacco plant from which the modified tobacco plant is derived. In an embodiment, the tobacco plant or a portion thereof generates a reduced level of at least one compound derived from the at least one endogenous amino acid having a reduced level as compared to an unmodified parent tobacco plant or a portion thereof. In an embodiment, the tobacco plant or a portion thereof generates a reduced level of at least one compound derived from the at least one endogenous amino acid having a reduced level as compared to an unmodified parent tobacco plant or a portion thereof upon heating and/or burning of the tobacco.

For example, in certain embodiments, the invention may comprise a method for producing a modified tobacco plant comprising a reduced level of at least one endogenous amino acid as compared to an unmodified tobacco plant from which the modified tobacco plant is derived comprising the steps of: incubating a seed or seeds (i.e., seed(s)) (i.e., at least one seed) from the unmodified tobacco plant in a solution comprising a mutagen; washing the seed(s) free of the mutagen; exposing the M0 seed(s) to a selection agent; germinating the seed(s) and growing at least one M0 tobacco seedling or seedlings (i.e., seedling(s)) in the presence of a selection agent; growing the M0 tobacco seedling(s) to generate at least one M0 tobacco plant comprising M1 tobacco seed(s), wherein the M1 tobacco seed(s) from the M0 tobacco plant comprise at least one mutagenized M1 tobacco seed; and germinating at least one mutagenized M1 tobacco seed to select for at least one modified M1 tobacco plant comprising reduced levels of at least one endogenous amino acid as compared to the unmodified tobacco plant. In certain embodiments, the method may further comprise the steps of: growing the at least one M1 tobacco plant to generate M2 tobacco seeds, wherein the at least one M1 tobacco plant is a homozygote for a mutation conferring the ability to grow in the presence of the selection agent. The M0, M1 and/or M2 plants may, in certain embodiments, be grown in the presence of a selection agent.

A variety of selection agents may be used for each of the methods, plants and compositions (e.g., tobacco products) of the invention. In one embodiment, the selection agent is an amino acid. For example, the selection agent may be leucine. Or, other amino acids may be used as a selection agent. In certain embodiments, the selection agent is an amino acid other than lysine and/or threonine.

In an embodiment, the modified tobacco plant is the species *Nicotiana tabacum*.

In certain embodiments, the modified tobacco plants made by the methods of the invention may comprise at least one of the 10NH-18, 10N-23, 10NH-27, 10NH-34 or 10NH-9 lines, wherein a representative sample of seeds for these lines have been deposited with the American Type Culture Collection (ATCC, 10801 University Blvd., Manassas, Va. 20110-2209), on Dec. 22, 2011, under conditions prescribed by the Budapest Treaty, and which will have all restrictions on accessibility of the seeds irrevocably removed upon issuance of a patent. The deposited seeds have been assigned ATCC Accession Numbers PTA-12339 (10NH-23), PTA-12340 (10NH-34), PTA-12341 (10NH-18), PTA-12342 (10NH-27), and PTA-12343 (10NH-9), respectively.

In yet other embodiments, the invention may comprise a modified tobacco plant or a portion thereof comprising a decrease in at least one endogenous amino acid as compared to an unmodified tobacco plant or portion thereof from which the plant is derived. In an embodiment, the tobacco plant or a portion thereof generates a reduced level of at least one compound derived from the at least one endogenous amino acid having reduced levels as compared to an unmodified parent tobacco plant or a portion thereof. In an embodiment, upon heating and/or burning, the tobacco plant or a portion thereof generates a reduced level of at least one compound derived from the at least one endogenous amino acid having reduced levels as compared to an unmodified parent tobacco plant or a portion thereof.

In an embodiment, the genome of the modified tobacco plant comprises an alloploid genome. Also, in an embodiment, the genome of the modified tobacco plant comprises a mutation that exhibits a dominant phenotype of resistance to growth in the presence of an excess of a selection agent (e.g., such as an amino acid). In an embodiment, the modified tobacco genome has a mutation that exhibits a dominant phenotype of resistance to growth in the presence of leucine.

In an embodiment, the plant may comprise a reduction in endogenous asparagine and/or glutamic acid as compared to an unmodified plant. Or, as described herein, other amino acids may be reduced.

The reduction in the amino acid may result in reduced levels of compound made from the amino acid. In an embodiment, the tobacco plant or a portion thereof generates reduced levels of acrylamide and/or acrylonitrile as compared to the unmodified tobacco plant or a portion thereof upon heating and/or burning. For example, the plant or part thereof may comprise at least a 10, 20, 30, 40, 50, 60, 70, 80, 90 or 99% reduction in acrylamide and/or acrylonitrile upon heating and/or burning of the tobacco plant or a portion thereof as compared to an unmodified plant.

In an embodiment, the modified tobacco plant is the species *Nicotiana tabacum*. In certain embodiments, the modified tobacco plants may comprise at least one of the 10NH-5, 10NH-18, 10N-23, 10NH-27, 10NH-34 or 10NH-9 lines.

In other embodiments, the present invention comprises a modified tobacco plant or a portion thereof comprising a decrease in the level of at least one of acrylamide and/or acrylonitrile as compared to an unmodified tobacco from which the plant is derived. In certain embodiments, the modified plant comprises a reduction in acrylamide and/or acrylonitrile upon heating and/or burning of the tobacco plant or a portion thereof as compared to the unmodified plant. Additionally and/or alternatively, the plant may comprise a reduction in the level of at least one endogenous amino acid as compared to the unmodified plant. For example, the modified plant may comprise a reduction in asparagine and/or glutamic acid as compared to the unmodified plant.

In an embodiment, the modified tobacco plant is the species *Nicotiana tabacum*. In certain embodiments, the modified tobacco plants may comprise at least one of the 10NH-5, 10NH-18, 10N-23, 10NH-27, 10NH-34 or 10NH-9 lines.

In certain embodiments, the modified tobacco plant is generated by mutagenesis. The method may, in certain embodiments, comprise the steps of: incubating a seed or seeds from the unmodified tobacco plant in a solution comprising a mutagen; washing the seed or seeds free of the mutagen; exposing the at least one M0 tobacco seed to a selection agent (e.g., adding the selection agent to soil or a medium in which the seed is at least partially immersed); germinating the seed or seeds in the presence of the selection agent and growing at least one M0 tobacco seedling; growing the at least one M0 tobacco seedling to generate at least one M0 tobacco plant comprising M1 tobacco seeds, wherein the M1 tobacco seeds from the M0 tobacco plant comprise at least one mutagenized M1 tobacco seed; and germinating the at least one mutagenized M1 tobacco seed to select for a modified M1 tobacco plant comprising reduced levels of at least one endogenous amino acid as compared to the unmodified tobacco plant (i.e., the M0 plant) from which the modified (i.e., M1) plant is derived. In certain embodiments, the method may comprise germinating the M1 and/or M2 plants derived from the at least one M1 plant in a medium comprising a selection agent. In certain embodiments, the amino acid having a reduced level is at least one of alanine, asparagine, glutamic acid, glutamine, proline, histidine, lysine, phenylalanine and/or serine. In an embodiment, the amino acid having a reduced level is asparagine. In another embodiment, the amino acid having a reduced level is glutamic acid. Or, other amino acids may be reduced.

In yet other embodiments, the invention may comprise a tobacco product comprising a modified tobacco from a plant having a reduced level of at least one endogenous amino acid as compared to an unmodified tobacco plant from which the modified tobacco plant is derived. In certain embodiments, the modified plant is generated using the methods described herein. In an embodiment, the tobacco product generates a reduced level of a compound derived from the at least one endogenous amino acid amino acid as compared to a product comprising an unmodified parent tobacco plant or a portion thereof. In an embodiment, upon heating and/or burning, the tobacco product generates a reduced level of a compound derived from the at least one endogenous amino acid as compared to a product comprising an unmodified parent tobacco plant or a portion thereof.

In an embodiment, the genome of the modified tobacco used in the tobacco product comprises an alloploid genome. Also, in an embodiment, the genome of the modified tobacco plant comprises a mutation that exhibits a dominant phenotype of resistance to growth in the presence of an excess of an amino acid selection agent, such as, but not limited to, leucine In certain embodiments, the tobacco product may comprise a modified tobacco comprising a decrease in acrylamide levels and/or acrylonitrile levels. The reduced levels of acrylamide and/or acrylonitrile may be occur upon heating and/or burning of the tobacco as compared to an unmodified tobacco. For example, the plant or part thereof may comprise at least a 10, 20, 30, 40, 50, 60, 70, 80, 90 or 99% reduction in acrylamide and/or acrylonitrile upon heating and/or burning of the tobacco product as compared to a tobacco product with tobacco from the unmodified plant.

In certain embodiments, the tobacco comprises a reduction in the endogenous levels of at least one amino acid In certain embodiments, the amino acid with decreased levels is asparagine and/or glutamic acid. Or other amino acids such as alanine, and/or glutamine and/or proline may be reduced. Or, other amino acids such as histidine, lysine, phenylalanine and/or serine may be reduced. Or, other amino acids may be reduced.

In an embodiment, the modified tobacco plant is the species *Nicotiana tabacum*. In certain embodiments, the modified tobacco plants may comprise at least one of the 10NH-5, 10NH-18, 10N-23, 10NH-27, 10NH-34 or 10NH-9 lines.

In certain embodiments, the invention may also comprise a tobacco product comprising tobacco from a modified tobacco plant, the tobacco having a reduced in level of acrylamide and/or acrylonitrile and/or other non-natural chemicals as compared to an unmodified tobacco from which the plant is derived. In certain embodiments, the modified plant is generated using the methods described herein. In certain embodiments, the invention may also comprise a tobacco product comprising tobacco from a modified tobacco plant, the tobacco having a decrease in levels of acrylamide and/or acrylonitrile and/or other non-natural chemicals as compared to an unmodified tobacco from which the plant is derived upon heating and/or burning of the tobacco plant or a portion thereof.

In an embodiment, the genome of the modified tobacco used in the tobacco product comprises an alloploid genome. Also, in an embodiment, the genome of the modified tobacco plant comprises a mutation that exhibits a dominant phenotype of resistance to growth in the presence of an excess of an amino acid selection agent, such as, but not limited to, leucine.

In certain embodiments, the tobacco product may comprise a modified tobacco comprising a decrease in acrylamide levels and/or acrylonitrile levels. The reduced levels of acrylamide and/or acrylonitrile may be occur upon heating and/or burning of the tobacco as compared to an unmodified tobacco. For example, the plant or part thereof may comprise at least a 10, 20, 30, 40, 50, 60, 70, 80, 90 or 99% reduction in acrylamide and/or acrylonitrile upon heating and/or burning of the tobacco product as compared to a tobacco product with tobacco from the unmodified plant.

In certain embodiments, the tobacco comprises a reduction in the endogenous levels of at least one amino acid In certain embodiments, the amino acid with decreased levels is asparagine and/or glutamic acid. Or other amino acids such as alanine, and/or glutamine and/or proline may be reduced. Or, other amino acids such as histidine, lysine, phenylalanine and/or serine may be reduced. Or, other amino acids may be reduced.

In an embodiment, the modified tobacco plant is the species *Nicotiana tabacum*. In certain embodiments, the modified tobacco plants may comprise at least one of the 10NH-5, 10NH-18, 10N-23, 10NH-27, 10NH-34 or 10NH-9 lines.

In yet other embodiments, the invention comprises tobacco from at least one of the 10NH-5, 10NH-18, 10N-23, 10NH-27, 10NH-34 or 10NH-9 lines.

Thus, in some embodiments, the present invention comprises tobacco products made from the plants and tobacco lines of the invention. For example, in certain embodiments, the present invention comprises tobacco products comprising a modified tobacco from tobacco plants having a reduced level of non-natural chemicals as compared to an unmodified tobacco. In certain embodiments, the present invention comprises tobacco products comprising a modified tobacco from a tobacco plant having a reduced level of acrylamide and/or acrylonitrile and/or other non-natural chemicals upon heating and/or burning of the tobacco as compared to an unmodified tobacco. Also, the tobacco products of the invention may comprise a tobacco product comprising a modified tobacco having a reduced level of at least one endogenous amino acid as compared to an unmodified tobacco from which the modified tobacco is derived. In an embodiment, the amino acid having a reduced level is at least one of alanine, asparagine, glutamic acid, glutamine, proline, histidine, lysine, phenylalanine and/or serine. In an embodiment, the amino acid having a reduced level is asparagine. Additionally or alternatively, the amino acid having a reduced level is glutamic acid. Or, other amino acids may be reduced.

The reduction of certain amino acids may be associated with a reduction in non-natural chemicals that can be generated upon heating and/or burning (e.g., smoking) the tobacco.

For example, acrylamide is a carcinogen that may be found in cigarette smoke. In certain embodiments, decreasing asparagine levels in tobacco may be correlated with decreased levels of acrylamide formation in smoke. Thus, in certain embodiments, the methods and/or tobacco plants and/or tobacco products of the invention may be used to make tobacco products that upon heating and/or burning, generate reduced acrylamide and/or other chemicals that may be pyro-synthesized from amino acids.

In other embodiments, decreasing at least one of alanine, asparagine, glutamic acid, glutamine, proline, histidine, lysine, phenylalanine and/or serine may be associated with a reduction in another potential carcinogen, acrylonitrile. In an embodiment, the reduction of glutamic acid can be associated with a reduction in acrylonitrile. Thus, in certain embodiments, the methods and/or tobacco plants and/or tobacco products of the invention may be used to make tobacco products that upon heating and/or burning, generate reduced acrylonitrile and/or other chemicals that may be pyro-synthesized from amino acids.

For example, in certain embodiments, the present invention comprises a method for producing a modified tobacco plant comprising reduced levels of endogenous asparagine, such that upon heating and/or burning, the tobacco plant or a portion thereof generates reduced levels of acrylamide as compared to an unmodified parent tobacco plant or a portion thereof.

Also, in certain embodiments, the present invention comprises a method for producing a modified tobacco plant comprising a reduced level of at least one of endogenous alanine, asparagine, glutamic acid, glutamine, proline, histidine, lysine, phenylalanine and/or serine, such that the tobacco plant or a portion thereof generates reduced levels of acrylonitrile as compared to an unmodified parent tobacco plant or a portion thereof.

For example, in certain embodiments, tobacco plants and/or products of the present invention have tobacco leaves or other portions of the plant that upon heat treatment, produce about 0.33 micrograms (µg) of asparagine per milligram of dry plant weight, or about a 70% decrease or more over the parent tobacco plants from which the modified tobacco plant is derived.

Also, in certain embodiments, the amount of acrylamide in smoke generated from tobacco leaves or other portions of the modified tobacco plants of the present invention is about 50% or less as compared to cigarette smoke generated from other types of tobacco leaves generally used for tobacco products plants and/or plants from which the modified tobacco plant is derived.

For example, in certain embodiments, tobacco plants and/or products of the present invention have tobacco leaves or other portions of the plant that upon heat treatment, produce less than about 0.110 micrograms (µg) of glutamic acid per milligram of dry plant weight, or about a 40% or more decrease as compared to the parent tobacco plants from which the modified tobacco plant is derived.

Also, in certain embodiments, the amount of acrylonitrile in smoke generated from tobacco leaves or other portions of the modified tobacco plants of the present invention is about 50% as compared to cigarette smoke generated from other types of tobacco leaves generally used for tobacco products and/or plants from which the modified tobacco plant is derived.

As described in more detail herein, in certain embodiments for each of the methods, plants and tobacco products of the invention, the modified tobacco plant is the species *Nicotiana tabacum*. Or, other plants or tobaccos may be used.

In certain embodiments, the modified tobacco used in the tobacco products of the invention may comprise tobacco from at least one of the 10NH-5, 10NH-18, 10N-23, 10NH-27, 10NH-34 or 10NH-9 lines.

Methods of Making Tobacco Having a Reduced Content of at Least One Amino Acid

Embodiments of the present invention provide methods of making plants having a significantly decreased level of at least one endogenous amino acid. In certain embodiments, the present invention provides methods of making tobacco plants (or tobacco lines derived from such plants) having a significantly decreased level of at least one amino acid.

In certain embodiments, the endogenous amino acid with a decreased level is at least one of alanine, asparagine, glutamic acid, glutamine, proline, histidine, lysine, phenylalanine and/or serine. In an embodiment, the endogenous amino acid having a reduced level is asparagine. Additionally or alternatively, the endogenous amino acid having a reduced level is glutamic acid. Or, other amino acids may be reduced.

In an embodiment, heating and/or burning the tobacco plant or a portion thereof generates reduced levels of a compound derived from the amino acid targeted for reduction, as compared to an unmodified parent tobacco plant or a portion thereof. In certain embodiments, the modified tobacco plant or a portion thereof generates a reduced level of acrylamide and/or acrylonitrile and/or other non-natural chemicals (e.g., upon heating and/or burning) as compared to an unmodified parent tobacco plant or a portion thereof.

Thus, in one embodiment, the present invention comprises a method for producing a modified plant (or a line derived from the plant) comprising an altered phenotype of a significant reduction in particular amino acids by selection for a mutation of interest in the M0 generation. The method may comprise incubating seeds or plant tissue of the plant of interest in a solution comprising a mutagen. The method may also comprise washing the seeds free of the mutagen. Or, the seeds may be mutated by other methods (e.g., irradiation) and then the follow steps of the method performed.

The method may additionally comprise germinating the a seed or seeds and growing at least one M0 seedling. In an embodiment, the selection agent is added to the seed at this time. The method may further comprise adding a selection agent to the seedling or seedlings, wherein the selection agent selects for a chimeric M0 plant, wherein the M0 chimeric plant at least partially comprises the predetermined altered phenotype. The method may then comprise growing the M0 chimeric plant to generate M1 seeds, wherein the M1 seeds may comprise non-mutagenized M1 seeds and at least one mutagenized M1 seed comprising the predetermined altered phenotype, and germinating the M1 seeds to select for M1 plants comprising the predetermined altered phenotype. In certain embodiments, the method may further comprise growing the M1 plants to generate M2 seeds, wherein at least one of the M1 plants is a homozygote for a mutation causing the altered phenotype and germinating the M2 seeds to identify at least one homozygote M1 plant. In certain embodiments, the method may comprise germinating the M1 and/or M2 plants derived from the M1 plants in a medium and/or soil comprising a selection agent.

In alternate embodiments, the modified plant (or a line derived from the plant) has at least a 10, 20, 30, 40, 50, 60, 70, 80, 90 or 99% decrease in at least one amino acid. In alternate embodiments, the modified plant has at least a 1.2, 1.5, 2, 4, 6, 8, 10, 20, 50 or 100-fold reduction in at least one amino acid. In an embodiment, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels is glutamic acid. Or, other amino acids may be reduced.

In an embodiment, the tobacco plant or a portion thereof generates reduced levels of a compound derived from the amino acid targeted for reduction, as compared to an unmodified parent tobacco plant or a portion thereof. For example, in certain embodiments, the method comprises generating modified tobacco plants that upon heating and/or burning, generate reduced levels of acrylamide and/or acrylonitrile and/or other non-natural chemicals as compared to an unmodified parent tobacco plants.

For example, in certain embodiments, the present invention comprises a method for producing a modified tobacco plant comprising generating a tobacco plant comprising reduced levels of endogenous asparagine, such that upon heating and/or burning, the modified tobacco plant or a portion thereof generates reduced levels of acrylamide as compared to an unmodified parent tobacco plant or a portion thereof.

In other embodiments, the present invention comprises a method for producing a modified tobacco plant comprising generating a tobacco plant comprising reduced levels of at least one of endogenous alanine, asparagine, glutamic acid, glutamine, proline, histidine, lysine, phenylalanine and/or serine endogenous asparagine, such that upon heating and/or burning, the modified tobacco plant or a portion thereof generates reduced levels of acrylonitrile as compared to an unmodified parent tobacco plant or a portion thereof.

For the various mutagenesis methods of the invention, the tobacco plant comprises at least a 10% reduction in acrylamide levels upon heating and/or burning of the tobacco plant or a part of the tobacco plant. For example, in alternate embodiments, a product made from at least a portion of the modified tobacco plant, or a tobacco line derived from the plant, has at least a 10, 20, 30, 40, 50, 60, 70, 80, 90 or 99% decrease in acrylamide upon heating and/or burning (e.g., in smoke produced from the tobacco). In alternate embodiments, the modified tobacco line has at least a 1.2. 1.5, 2, 4, 6, 8, 10, 20, 50 or 100-fold reduction in acrylamide upon heating and/or burning (e.g., in smoke produced from the tobacco).

In certain embodiments of the methods of the invention, the amino acid having reduced levels is glutamic acid. Or, other selected amino acids may be reduced. For example, the tobacco plant may comprises at least a 10% reduction in glutamic acid levels. Also, in alternate embodiments, a product made from at least a portion of the modified tobacco plant, or a line derived from the tobacco plant, has at least a 20, 30, 40, 50, 60, 70, 80, 90 or 99% decrease in glutamic acid levels.

Also, in alternate embodiments, a product made from at least a portion of the modified tobacco plant, or a tobacco line derived from the plant, has at least a 10, 20, 30, 40, 50, 60, 70, 80, 90 or 99% decrease in acrylonitrile upon heating and/or burning (e.g., in smoke produced from the tobacco). In alternate embodiments, the modified tobacco line has at least a 1.2, 1.5, 2, 4, 6, 8, 10, 20, 50 or 100-fold reduction in acrylonitrile upon heating and/or burning (e.g., in smoke produced from the tobacco).

In embodiments for the method of producing a modified tobacco plant comprising a reduced level of at least one amino acid, and/or producing modified tobacco plants that upon heating and/or burning the plant or a portion thereof generate a reduced level of acrylamide and/or acrylonitrile and/or other non-natural chemicals as compared to an unmodified tobacco plants, the method may comprise the steps of: incubating at least one tobacco seed from an unmodified tobacco plant in a solution comprising a mutagen; washing the at least one seed free of the mutagen; exposing the at least one seed to a selection agent; germinating the at least one seed and growing at least one M0 tobacco seedling on a medium comprising a selection agent; growing the at least one M0 tobacco seedling to generate at least one M0 tobacco plant comprising M1 tobacco seeds, wherein the M1 tobacco seeds comprise at least one mutagenized M1 tobacco seed; and germinating the at least one mutagenized M1 tobacco seed to select for a modified M1 tobacco plant comprising reduced levels of at least one amino acid as compared to the unmodified tobacco plant. In certain embodiments, the method may further comprise growing the at least one M1 tobacco plant to generate M2 tobacco seeds, wherein the at least one M1 tobacco plant is a homozygote for a mutation causing the altered phenotype and germinating the M2 tobacco seeds to identify the at least one homozygote M1 tobacco plant. In certain embodiments, the method may comprise germinating the at least one M1 plant and/or at least one M2 plant derived from the M0 or M1 plants in soil or other type of medium comprising a selection agent.

Also in certain embodiments of the methods of the invention, a medium comprising at least one selection agent is added to M0 seedlings at certain developmental stages, as during a predetermined time period after germination. For tobacco (e.g., *Nicotiana tabacum*) a medium comprising at least one selection agent may be added to M0 seedlings 7 to 14 days after germination. For example, the second medium comprising at least one selection agent may be added to M0 seedlings about 10 days after germination. In alternate embodiments, the selection may be continuously present during growth of the M0 seedlings.

As discussed further herein, a variety of plants may be modified using the methods of the invention. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, as described herein, any of the genus of *Nicotiana* or blends thereof may be used. Such members are described in U.S. Patent Publication Nos. 2006/0185686 and 2011/0174323, the disclosures of which is incorporated by reference in its entirety herein. Or, other tobaccos may be used.

In certain embodiments, the mutagen is ethyl methanesulfonate (EMS). In some embodiments, the EMS comprises a final concentration of 0.01 to 2%. Or, the EMS may comprise a final concentration of 0.05 to 1%. Or, the EMS may comprise a final concentration of 0.2 to 0.7%. For example, in certain embodiments a concentration of 0.5% may be used. Or, other chemical mutagens (or irradiation) may be used.

In certain embodiments, the mutagenized seeds are suspended within solidified agar plates containing the selection agent. In other embodiments, seeds may be suspended in a nutrient medium and applied to a semi-permeable surface for growth prior to addition of the selection agent. Or, selection may be performed using a hydroponic system or in soil.

Thus, embodiments of the present invention comprise methods for plant mutagenesis that includes a selection step at the M0 chimeric stage. For example, in one aspect, the present invention comprises selection of plants comprising resistance to high (e.g., potentially lethal) amounts of leucine as a selection agent. Or, other selection agents (e.g., other amino acids) may be used. Or, other compounds that regulate amino acid synthesis or the metabolism of amino acids could be used.

In some embodiments, the selection agent (e.g. leucine) is present at a concentration ranging from 0.3 to 20 mM. Or, the selection agent (e.g., leucine) may be present at a concentration ranging from 0.5 to 10 mM. Or, the selection agent (e.g., leucine) may be present at a concentration ranging from 2.0 to 10.0 mM.

The M0 chimeric plant will, in certain embodiments, comprise a subpopulation of cells resistant to the selection agent; these cells may confer viability to the entire plant when the plant is grown in the presence of a selection agent such as, but not limited to, elevated levels of leucine. The present invention thus can eliminate the growth of a large population of the M0 plants for production of M1 seeds, thereby substantially reducing the number of progeny that must be screened at the M1 stage, to provide a cost-effective plant breeding program suitable for large plants, or plants comprising complex genomes, such as tobacco. The method used herein is distinct from the selection method used to produce *N. tabacum* lines comprising a significantly increased amino acid content, as described in U.S. Pat. Nos. 6,730,832, 7,173,170 and 7,825,305, the disclosures of which are incorporated by reference in their entireties herein.

Embodiments of the invention may also comprise seeds derived from modified plants that have been generated using the methods of the invention, wherein the seeds are capable of propagating the modified plant lines having reduced levels of at least one amino acid. In certain embodiments, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels may be glutamic acid. Or, other amino acids may be reduced Also, as discussed in more detail herein, the invention comprises tobacco products derived from plants and/or plant lines generated using the methods of the invention such as leaves for chewing tobacco, flue-cured leaves for smoking tobacco, and other known tobacco products. In certain embodiments, the present invention comprises methods for reducing the levels of a non-natural compound that may be present in the tobacco and/or generated upon heating and/or burning the tobacco and/or improving the flavor of a tobacco product, comprising generating a modified tobacco plant having a decrease in the concentration of at least one amino acid, mixing the modified tobacco with unmodified tobacco, and including the mixture in a tobacco product. Preferably, the modified tobacco plant is made by mutagenizing tobacco seeds and selecting for partially mutagenized chimeric plants. In certain embodiments, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels is glutamic acid. Or, other amino acids may be reduced.

Thus, embodiments the present invention relate to a utilization of a method for producing plants with an altered phenotype by selection at the M0 chimeric stage and the use of this method to product plants having a decrease in at least one amino acid. Mutagenesis has been used as a conventional breeding method to develop improved cultivars of a number crops, including tobacco (see e.g. A. M. van Harten, *Mutation Breeding: Theory and Practical Applications*, pp. 1-63, Cambridge Univ. Press, New York, N.Y., 1998). Generally, the target plant materials used to develop desired mutant using chemical mutagens are classified into two categories: (1) seed and (2) tissue or cell culture.

For example, seeds may be treated with specific mutagens, and the surviving seeds grown to produce their progenies (e.g. Heremans and Jacobs, 1995). The generation that grows from the mutagenized seed is called the M0 generation, and the progeny collected from the M0 plants are the M1 generation, from which the desired mutants are usually selected. Further selection of plants which are homozygous for the mutation of interest may be made by growing progeny from M1 plants (i.e. the M2 generation) under selective conditions.

Although mutagenesis and selection is much easier to perform on tissue culture cells (e.g. Cattoir-Reynaerts et al., 1983; Dotson et al., 1990; Hibberd et al., 1980), the mutant cells or tissues must be regenerated to fertile plants. Establishment of a system for regeneration of a fertile plant from the genotype of interest can be time-consuming, expensive, and requires a high level of technical expertise. In addition, undesired somaclonal variation often occurs in regenerated mutants of interest as a result of autosomal chromosome duplications.

Genetic engineering has also been used produce transgenic plants. For example, expression of a bacterial AK in tobacco (*N. tabacum*) may result in overproduction of free threonine in (O. Shaul and G. Galili, 1992, *Plant Physiol.*, 100:1157-1163; Karchi, H., et al., 1993, *Plant J.*, 3: 721-727), canola, soybean and maize (Falco, S. C., et al., 1995, *Biotechnology* 13: 577-582; Falco, S. C., et al., 1997, *SIM News* 47: 53-57). Still, this approach can be technically demanding, requires introduction of foreign DNA into the genome, and does not generate the wide variety of mutants needed for propagation of a crop in various ecosystems. In addition, the effects of transgenic crops produced by genetic engineering on the long-term stability of ecosystems is not known (N. C. Ellstrand, 2001, *Plant Physiol.*, 125: 1543-1545). Finally, transgenic crops have not been widely accepted by the public, especially in European countries.

It is therefore an object of the present invention to utilize a screening method whereby the screening is at least in part performed using M0 plants. Referring now to FIG. 1, in one aspect, the invention provides a method of producing tobacco (e.g., *Nicotiana tabacum*) lines having a reduced amount of at least one endogenous amino acid. In an embodiment, the method comprises the steps of: (a) mutagenizing tobacco seeds 2 of in a solution containing the mutagen ethyl methane-sulfonate (EMS) 4 at a concentration of about 0.5% for 20 hrs; (b) washing the mutagenized seeds in water 6; (c) sterilizing the seeds 2 with 70% ethanol followed by 20% Chlorox bleach 8 on an agitating shaker 10; (d) rinsing with sterile water 6; (e) suspending the seeds 2 in nutrient medium with 0.1% Agar (a semi-solid colloidal suspension) 12; (f) applying about 0.750 ml of the suspension with about 50 seeds 2 onto a solidified phytoagar plate containing selection agent 16; (g) germinating the seeds and growing the seedlings 18 in a tissue culture room at 25° C. with a 16-h photoperiod from cool-white fluorescent lamps; (h) transplanting the healthy M0 seedlings 18 in soil and growing as M0 plants 22 in a greenhouse; and (i) planting individual M1 seeds 23 from M0 plants 22 in a field to grow M1 plants 24; (j) testing the M1 plants for lower than average levels of at least one amino acid (e.g., asparagine); (k) growing M2 seeds 25 from the M1 plants with a low level of at least one amino acid, and testing for M2 lines 26 producing lower than average levels of at least one amino acid (e.g., asparagine or another amino acid). These non-chimeric tobacco plants are generally a mixture of heterozygotes and homozygotes. An additional selection step may be added for selection of tobacco lines in the field based on chemical analysis of amino acid levels.

These modified plants and/or lines also provide the basis for the production of hybrid lines, utilizing as one or both parents, the novel lines of the present invention. Also within the scope of the present invention are clones, somaclones, and derivatives of the novel lines.

Tobacco Plants Having Reduced Levels of at Least One Amino Acid

In certain embodiments, the invention comprises plants having a significantly decreased level of at least one endogenous amino acid. In certain embodiments, the amino acid having a reduced level is at least one of alanine, asparagine, glutamic acid, glutamine, proline, histidine, lysine, phenylalanine and/or serine. In an embodiment, the endogenous amino acid having a reduced level is asparagine. Additionally or alternatively, the amino acid having a reduced level is glutamic acid. Or, other amino acids may be reduced.

In an embodiment, upon heating and/or burning, the tobacco plant or a portion thereof generates a reduced level of a compound derived from that amino acid, as compared to an unmodified parent tobacco plant or a portion thereto. For example, in certain embodiments, the tobacco plants of the invention have reduced levels of acrylamide and/or acrylonitrile and/or other non-natural chemicals upon heat-treatment of the plant or a part thereof.

As discussed further herein, a variety of plants may be modified. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, in certain embodiments, any of the genus of *Nicotiana* or other types of tobacco may be used. Such tobaccos are described in U.S. Patent Publication Nos. 2006/0185686 and 2011/0174323, the disclosures of which are incorporated by reference in their entireties herein. Or, other tobaccos may be used.

For example, in certain embodiments, the present invention may comprise a tobacco plant comprising a modified tobacco having reduced levels of at least one of alanine, asparagine, glutamic acid, glutamine, proline, histidine, lysine, phenylalanine and/or serine as compared to an unmodified tobacco plant from which the modified plant is derived. In an embodiment, the amino acid having reduced levels is asparagine. Additionally or alternatively, the amino acid having reduced levels is glutamic acid. Or, other amino acids may be reduced.

Additionally or alternatively, the present invention may comprise a tobacco plant comprising a reduced level of at least one amino acid as compared to an unmodified tobacco plant from which the modified plant is derived wherein the genome of the modified tobacco plant comprises an alloploid genome having a mutation that exhibits a dominant phenotype of resistance to growth in the presence of a selection agent such as an amino acid (e.g., leucine or another amino acid). Additionally or alternatively, the present invention may comprise a modified tobacco plant comprising a decrease in the levels of acrylamide and/or acrylonitrile and/or other non-natural chemicals (e.g., upon heating and/or burning of the tobacco plant or a portion thereof) as compared to an unmodified tobacco from which the plant is derived, wherein the genome of the modified tobacco plant comprises an alloploid genome having a mutation that exhibits a dominant phenotype of resistance to growth in the presence of a selection agent such as an amino acid (e.g., leucine or another amino acid).

The plants (e.g., tobacco plants) included in the present invention also include plants (and/or lines derived from such plants) which may be genetically engineered using foreign (e.g., non-tobacco) DNA at a locus distinct from the genes relating to production of the amino acid of interest (i.e., the amino acid for which decreased concentration in the tobacco is the end result). For example, tobacco plants which are genetically engineered to be resistant to pesticides and which are also modified by mutagenesis of tobacco genomic DNA (e.g., at the asparaginase, asparagine synthetase for plants having reduced asparagine, or other amino acid biosynthesis or metabolic loci) to become low asparagine producers and/or to comprise a reduced amount of acrylamide and/or acrylonitrile upon heating and/or burning of the tobacco plant or a portion thereof, are included in the present invention.

Thus, embodiments of the present invention may comprise a modified tobacco plant, or a tobacco line derived from the plant, having a decreased amount of at least one amino acid as compared to an unmodified parent tobacco plant and/or tobacco line from which the modified plant is derived, wherein the genome of the modified tobacco plant consists of, or consists essentially of, plant DNA. Preferably, the genome of the modified tobacco plant consists of, or consists essentially of, tobacco DNA. Even more preferably, the genes of the modified tobacco plant related to the biosynthesis and/or metabolism of the amino acid targeted for reduction (e.g., asparaginase and/or asparagine synthetase for plants with reduced asparagine or other amino acid biosynthesis or metabolic loci) consists of, or consists essentially of, tobacco genomic DNA.

The present invention also includes a modified tobacco plant and/or a tobacco line derived from the plant having an decreased amount of at least one amino acid and/or a reduced amount of acrylamide and/or acrylonitrile and/or other non-natural chemicals (e.g., upon heating and/or burning of the tobacco plant or a portion thereof), as compared to an unmodified parent tobacco line from which the modified plant is derived, wherein the modified plant has consists of, or consists essentially of, the same antibiotic resistance as the unmodified parent line. In certain embodiments, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels may be glutamic acid. Or, other amino acids may be reduced.

In yet another aspect, the present invention comprises a modified tobacco plant, or a tobacco line derived from the plant, having an below-average amount of at least one amino acid as compared to an unmodified parent tobacco plant, wherein the genome of the modified tobacco plant consists of, or consists essentially of, plant DNA, or wherein the modified tobacco plant is produced by the steps of mutagenesis of tobacco genomic DNA and selection of M0 plants having a mutation of interest. For example, the present invention comprises a modified tobacco plant and/or a tobacco line derived from the plant having a below-average amount of at least one amino acid as compared to an unmodified parent tobacco plant or plant line, wherein the genes of the modified tobacco plant related to the biosynthesis and/or metabolism of the amino acid targeted for reduction (e.g., asparaginase and/or asparagine synthetase for plants with reduced asparagine) consists of, or consists essentially of, tobacco genomic DNA. More preferably, the asparaginase gene of the modified tobacco plant consists of, or consists essentially of tobacco genomic DNA.

In another aspect, the present invention comprises a modified tobacco plant and/or a tobacco line derived from the tobacco plant having a reduced amount of at least one amino acid as compared to an unmodified parent tobacco line, wherein the tobacco plant is produced by mutagenesis of tobacco genomic DNA and selection of M0 plants having a mutation of interest. In an embodiment, the tobacco plant is produced by the steps of: mutagenizing a tobacco seed(s); exposing the M0 seeds to a selection agent; germinating the mutagenized seed(s) in the presence of the selection agent (e.g., leucine) and growing at least one M0 seedling; growing at least one chimeric M0 plant to generate M1 seeds, wherein the M1 seeds from the M0 plant may comprise non-mutagenized M1 seeds and at least one mutagenized M1 seed; and germinating the M1 seeds in medium to select for mutagenized M1 plants. In certain embodiments, the method of preparing the modified plant includes the steps of growing the M1 tobacco plants to generate M2 seeds, wherein at least one of the M1 plants is a homozygote for a mutation conferring the ability to grow in the presence of increased a selection agent (e.g., leucine); and germinating the M2 seeds to identify at least one homozygote M1 plant. In certain embodiments, the method may comprise germinating the at least one M1 plant and/or at least one M2 plant derived from the M1 plants in a medium (or soil) comprising a selection agent.

In alternate embodiments, the modified plant (or a line derived from the plant) has at least a 10, 20, 30, 40, 50, 60, 70, 80, 90 or a 99% decrease in at least one amino acid. In alternate embodiments, the modified plant has at least a 1.2, 1.5, 2, 4, 6, 8, 10, 20, 50 or 100-fold reduction in at least one amino acid. In an embodiment, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels is glutamic acid. Or, other amino acids may show a reduction.

In certain embodiments for each of the plants of the invention, the modified tobacco plant comprises at least a 10% reduction in acrylamide and/or acrylonitrile and/or other non-natural chemicals levels upon heating and/or burning of the tobacco plant or a part of the tobacco plant. Also, in alternate embodiments, the modified tobacco plant, or a tobacco line derived from the plant, has at least a 20, 30, 40, 50, 60, 70, 80, 90, or 99% decrease in acrylamide and/or acrylonitrile and/or other non-natural chemicals upon heating and/or burning the plant or a portion of the plant (e.g., in smoke produced from leaves from a modified tobacco plant of the invention). In alternate embodiments, the modified tobacco plant or a portion thereof has at least a 1.2, 1.5, 2, 4, 6, 8, 10, 20, 50 or 100-fold reduction in acrylamide and/or acrylonitrile and/or other non-natural chemicals upon heating and/or burning (e.g., in smoke produced from the tobacco).

Also, for each of the plants and/or tobacco lines, embodiments of the invention may comprise seeds capable of propagating the modified plants and/or lines having an reduced amount of at least one amino acid and/or a reduction in acrylamide and/or acrylonitrile and/or other non-natural chemicals upon heating and/or burning of the plant or a portion thereof. Such seeds, and deposits of such seeds are disclosed herein.

Thus, in certain embodiments, the present invention provides tobacco plants and/or lines derived from such plants that have been mutated so as to produce a reduced levels (i.e., concentration) of at least one amino acid.

In certain embodiments, these novel lines produce 0.332-0.810 micrograms (m) asparagine per milligram of dry weight of tobacco in cured leaf. This may represent about a 1.2 to 3.35 fold decrease in asparagine over the unmodified flue-cured *N. tabacum* parent, which normally yields a maximum of about 1.158 μg asparagine per milligram of dry weight of tobacco. The absolute amount of a specific amino acid may be dependent on processing of the leaf, or the developmental stage of the plant.

In certain embodiments, these novel tobacco lines produce <0.11 micrograms (m) glutamic acid per milligram of dry weight of tobacco in cured leaf. This may represent at least about a 1.3 fold decrease in glutamic acid over the unmodified flue-cured *N. tabacum* parent, which normally yields a maximum of about 0.15 μg per milligram of dry weight of tobacco. The absolute amount of a specific amino acid may be dependent on processing of the leaf, or the developmental stage of the plant.

Or, these novel lines may produce about 0.358 micrograms (m) glutamine per milligram of dry weight of tobacco in cured leaf. This may represent about a 2.5 fold decrease in glutamic acid over the unmodified flue-cured *N. tabacum* parent, as compared to a control value of about 0.9 μg per milligram of dry weight of tobacco. The absolute amount of a specific amino acid may be dependent on processing of the leaf, or the developmental stage of the plant.

Or, these novel lines may produce about 0.5 micrograms (m) alanine per milligram of dry weight of tobacco in cured leaf. This may represent about a 1.25 fold decrease in alanine over the unmodified flue-cured *N. tabacum* parent, which normally yields a maximum of about 0.63 μg per milligram of dry weight of tobacco. The absolute amount of a specific amino acid may be dependent on processing of the leaf, or the developmental stage of the plant.

Or, these novel lines may produce about 5 micrograms (μg) proline per milligram of dry weight of tobacco in cured leaf. This may represent about a 1.4 fold decrease in proline over the unmodified flue-cured *N. tabacum* parent, which normally yields a maximum of about 7.1 μg per milligram of dry weight of tobacco. The absolute amount of a specific amino acid may be dependent on processing of the leaf, or the developmental stage of the plant.

Tobacco Products of the Invention

In certain embodiments, the invention comprises products made from plants having a significantly decreased level of at least one endogenous amino acid.

In an embodiment, the amino acid having a reduced level is at least one of alanine, asparagine, glutamic acid, glutamine, proline, histidine, lysine, phenylalanine and/or serine. In an embodiment, the amino acid having a reduced level is asparagine. Additionally or alternatively, the amino acid having a reduced level may be glutamic acid. Or, other amino acids may show a reduction.

In an embodiment, upon heating and/or burning, the tobacco plant or a portion thereof generates reduced levels of a compound derived from the amino acid targeted for reduction, as compared to an unmodified parent tobacco plant or a portion thereof For example, in certain embodiments, and the plants and/or products made from the plants have reduced levels of acrylamide and/or acrylonitrile and/or other non-natural chemicals upon heat-treatment and/or burning of the plant or a portion thereof.

For example, in certain embodiments, the present invention may comprise a tobacco product comprising a modified tobacco from a modified tobacco plant, the modified tobacco plant having reduced levels of asparagine as compared to an unmodified tobacco plant from which the modified tobacco plant is derived. Additionally or alternatively, in certain embodiments, the present invention may comprise a tobacco product comprising a modified tobacco from a modified tobacco plant, the modified tobacco plant having reduced levels of acrylamide upon heating and/or burning the tobacco as compared to an unmodified tobacco from which the modified tobacco plant is derived.

Additionally or alternatively, the present invention may comprise a tobacco product comprising a modified tobacco from a modified tobacco plant, the modified tobacco plant having reduced levels of at least one amino acid as compared to an unmodified tobacco plant from which the modified tobacco plant is derived wherein the genome of the modified tobacco plant comprises an alloploid genome. In an embodiment, the modified tobacco may have a mutation that exhibits a dominant phenotype of resistance to growth in the presence of leucine (or another selection agent). In an embodiment, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels may be glutamic acid. Or, other amino acids may show a reduction.

Additionally or alternatively, the present invention may comprise a tobacco product made from a modified tobacco plant comprising a decrease in acrylamide and/or acrylonitrile and/or other non-natural chemicals levels upon heating and/or burning of the tobacco plant or a portion thereof as compared to an unmodified tobacco plant from which the modified plant is derived, wherein the genome of the modified tobacco plant comprises an alloploid genome having a mutation that exhibits a dominant phenotype of resistance to growth in the presence of leucine (or another selection agent).

In alternate embodiments, the tobacco product has at least a 10, 20, 30, 40, 50, 60, 70, 80, 90 or 99% decrease in at least one amino acid as compared to non-modified tobacco. In alternate embodiments, the tobacco product has at least a 1.2, 1.5, 2, 4, 6, 8, 10, 20, 50 or 100-fold reduction in at least one amino acid. In an embodiment, the amino acid having reduced levels is at least one of alanine, asparagine, glutamic acid, glutamine, proline, histidine, lysine, phenylalanine and/or serine. In an embodiment, the amino acid having reduced levels is asparagine. Additionally or alternatively, the amino acid having reduced levels may be glutamic acid. Or, other amino acids may show a reduction.

In certain embodiments, the tobacco product comprises at least a 10% reduction in acrylamide and/or acrylonitrile and/or other non-natural chemical levels upon heating and/or burning of the tobacco. Also, in alternate embodiments, the tobacco product has at least a 20, 30, 40, 50, 60, 70, 80, 90, or 99% decrease in acrylamide and/or acrylonitrile and/or other non-natural chemicals upon heating and/or burning the tobacco. In alternate embodiments, the tobacco product has at least a 1.2, 1.5, 2, 4, 6, 8, 10, 20, 50, or 100-fold reduction in acrylamide and/or acrylonitrile and/or other non-natural chemicals upon heating and/or burning (e.g., in smoke produced from the tobacco).

In embodiments of the products of the invention, the amino acid having reduced levels is asparagine. Or, other selected amino acids may be reduced. For example, the tobacco product may comprise at least a 10% reduction in asparagine levels. Also, in alternate embodiments, a product made from at least a portion of the modified tobacco plant, or a line derived from the tobacco plant, has at least a 20, 30, 40, 50, 60, 70, 80, 90 or 99% decrease in asparagine levels.

In certain embodiments, the product may comprise at least a 10% reduction in acrylamide levels upon heating and/or burning of the product. For example, in alternate embodiments, a product made from at least a portion of the modified tobacco plant, or a tobacco line derived from the plant, has at least a 20, 30, 40, 50, 60, 70, 80, 90 or 99% decrease in acrylamide upon heating and/or burning (e.g., in smoke produced from the tobacco). In alternate embodiments, the product made from a modified tobacco plant has at least a 1.2, 1.5, 2, 4, 6, 8, 10, 20, 50 or 100-fold reduction in acrylamide upon heating and/or burning (e.g., in smoke produced from the tobacco).

As discussed further herein, a variety of tobacco plants may be modified to generate products of the invention. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, in certain embodiments, any of the genus of *Nicotiana* or other tobaccos may be used in the tobacco products of the present invention. Such tobaccos are described in U.S. Patent Publication Nos. 2006/0185686 and 2011/0174323, the disclosures of which are incorporated by reference in its entirety herein. Or, other tobaccos and blends may be used in the tobacco products of the present invention. Also, included are all intraspecific and interspecifc hybrids of *Nicotiana* species.

In certain embodiments of the invention, different parts of the plant and/or individual tobacco grades may be evaluated for the level of acrylamide and/or acrylonitrile and/or other non-natural chemicals in smoke. For example, in certain embodiments, upper stalk grades may generate more acrylamide than lower stalk grades. Also, burley and oriental grades may generate more acrylamide than flue-cured grades.

In certain embodiments, the invention provides a heat-treated tobacco composition. As used herein, the terms "heated," "heating," or "heat-treated" with respect to tobacco refers to a tobacco material that has been thermally processed at an elevated temperature, such as a temperature of at least about 60° C., more typically at least about 100° C., for a time sufficient to alter the character or nature of the tobacco composition, such as at least about 10 minutes. In some cases, the heat treatment process alters the chemistry or sensory characteristics (e.g., taste and aroma) of the tobacco composition. The heat treatment process of the invention can be a modified version of conventional tobacco treatment processes, such as processes adapted to form flavorful and aromatic compounds (e.g., Maillard reaction products), processes adapted for pasteurization of tobacco compositions, processes for preparing tobacco casing products, reconstituted tobacco processes (e.g., cast sheet and paper-making reconstituted tobacco processes), tobacco extraction processes, reordering processes, toasting processes, steam treatments, and drying processes.

Heated or heat-treated tobacco products that may be generated using the tobacco plants and/or tobacco lines of the present invention are described in U.S. Patent Publication No. US 2011/0048434, the disclosure of which is incorporated by reference in its entirety herein. Thus, the heat-treated tobacco compositions of the invention can be used as an additive for a smoking article, or as a smokeless tobacco composition, such as loose moist snuff, loose dry snuff, chewing tobacco, pelletized tobacco pieces, extruded or formed tobacco strips, pieces, rods, or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips, or capsule-like materials.

Tobaccos used in the tobacco products of the invention may vary and generally the methods of the invention may be used on wild tobaccos or tobaccos that have been genetically modified in some manner. For example, the tobaccos used in the tobacco products of the invention may include most types of tobaccos such as flue-cured tobacco, burley tobacco, sun-cured tobacco (e.g., Oriental tobacco or Indian Kurnool), Maryland tobacco, dark tobacco, dark-fired tobacco, dark air cured (e.g., passanda, cubano, jatin and bezuki tobaccos) or light air cured (e.g., North Wisconsin and galpoa tobaccos), and Rustica tobaccos, as well as other rare or specialty tobaccos or even green or uncured tobaccos. Representative Oriental tobaccos include katerini, prelip, komotini, xanthi and yambol tobaccos.

Tobacco products used in the present invention, including tobacco compositions intended to be used in a smokeless form, may incorporate a single type of tobacco (e.g., in a so-called "straight grade" form). For example, the tobacco within a tobacco product may be composed solely of a genetically modified flue-cured tobacco (e.g., all of the tobacco may be composed, or derived from, either flue-cured tobacco lamina or a mixture of flue-cured tobacco lamina and flue-cured tobacco stem). The tobacco within a tobacco product also may have a so-called "blended" form. For example, the tobacco within a tobacco product of the present invention may include a mixture of parts or pieces of a flue-cured tobacco of the invention mixed with a burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts of a genetically modified flue cured tobacco of the invention (e.g., stem, lamina, or lamina and stem) on a dry weight basis. Other exemplary tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other exemplary tobacco blends incorporate about 20 to about 30 parts Oriental tobacco and about 70 to about 80 parts flue-cured tobacco. Or, other tobaccos or tobacco blends, such as those described in U.S. Patent Publication No. 2006/0185686 and 2011/0174323, the disclosures of which are incorporated by reference in their entireties herein may be used. Or, other blends may be used.

The relative amount of tobacco within the tobacco product may vary. Preferably, the amount of tobacco within the tobacco product ranges from at least about 10 percent or at least about 25 percent, on a dry weight basis. In certain instances, the amounts of other components within the tobacco product may exceed about 40 percent, on a dry weight basis. A typical range of tobacco material in the tobacco product may range from about 10 to about 60 weight percent, more often about 20 to about 40 weight percent on a dry basis. For example, the tobacco product may include additional flavorants, fillers, binders, buffering agents, colorants, and humectants.

The tobacco products of the present invention may be formulated as various articles of manufacture. For smokeless tobacco products, the tobacco compositions of the invention can be formed into desired product shapes. The method and apparatus used to form the tobacco product will depend on the desired shape. For example, the tobacco product can have the form of compressed tobacco pellets, multi-layered extruded pieces, extruded or formed rods or sticks, compositions having one type of tobacco formulation surrounded by a different type of tobacco formulation, rolls of tape-like films, readily water-dissolvable or water-dispersible films or strips, or capsule-like materials possessing an outer shell (e.g., a pliable or hard outer shell that can be clear, colorless, translucent or highly colored in nature) and an inner region possessing tobacco or tobacco flavor.

The tobacco products of the invention may be useful as additives for the manufacture of smoking articles. The tobacco of the invention can be incorporated into the tobacco blends, representative cigarette components, and representative cigarettes manufactured therefrom. For example, the tobacco leaves of the present invention can be incorporated into a smoking article as part of the smokable material charge. Or, the tobacco of the invention can be incorporated into a cigarette filter (e.g., in the filter plug, plug wrap, or tipping paper) or incorporated into cigarette wrapping paper, preferably on the inside surface, during the cigarette manufacturing process.

In certain embodiments of the tobacco products of the invention, the resulting smoking article is characterized by a reduced levels of acrylamide and/or acrylonitrile and/or other non-natural chemicals in mainstream smoke during use. For example, the smoking article can be characterized by a reduction in acrylamide and/or acrylonitrile and/or other non-natural chemicals in mainstream smoke relative to an untreated control smoking article (i.e., a comparable smoking article except containing no tobacco genetically modified according to the invention) of at least about 10 percent, at least about 20 percent, at least about 30 percent, at least about 40 percent, at least about 50 percent, at least about 60 percent, at least about 70 percent, at least about 80 percent, or more. In other words, the smoking article of the invention, such as a cigarette, containing the genetically modified tobacco composition of the invention can produce a reduced amount of acrylamide and/or acrylonitrile and/or other non-natural chemicals by weight in mainstream smoke as compared to an unmodified control smoking article smoked using the same smoking machine and under the same smoking conditions, such as the smoking machines and smoking conditions set forth in ISO 3308:1991 and ISO 4387:1991, which are incorporated by reference herein.

For example, in certain embodiments, the present invention provides products made from tobacco that has been mutated so as to produce a reduced levels (i.e., concentration) of acrylamide. Specifically, these tobacco products may produce, upon smoking, 0.038-0.045 micrograms (μg) acrylamide per milligram of dry weight of tobacco in cured leaf. This may represent about a 1.8-1.5 fold decrease in acrylamide over unmodified flue-cure tobacco, which normally yields a maximum of about 0.067 μg per milligram of dry weight of tobacco. The absolute amount of acrylamide generated may be dependent on processing of the leaf, the developmental stage of the plant, and/or the curing regime.

Also, in certain embodiments, the present invention provides products made from tobacco that has been mutated so as to produce a reduced levels (i.e., concentration) of acrylonitrile. Specifically, these tobacco products may produce, upon smoking, about 0.146 micrograms (μg) acrylonitrile per milligram of dry weight of tobacco in cured leaf. This may represent as much as a 2.2 fold decrease in acrylonitrile over unmodified flue-cure tobacco, which normally yields a maximum of about 0.331 μg per milligram of dry weight of tobacco. The absolute amount of acrylamide generated may be dependent on processing of the leaf, the developmental stage of the plant, and/or the curing regime.

The present invention may be better understood by reference to the following non-limiting examples.

EXAMPLE 1—Mutation of Tobacco

The present invention has been used to prepare several lines of N. tobacum having reduced amounts of certain amino acids.

Production of the EMS mutagenized breeding lines having increase threonine was previously described (see U.S. Pat. No. 6,730,832). Seed from a representative flue-cured tobacco (i.e., Sp227), was mutagenized with 0.5% EMS and designated as M0. To generate tobacco having decreased amino acid concentration, various (i.e., about 10 separate) aliquots Sp227 N. tabacum seeds were incubated in a solution containing ethyl methane sulfonate (EMS) at a concentration of about 0.5% for 20 hrs. Both K326 seeds and non-mutagenized Sp227 seeds were used as the control. The treated seeds were then washed with MiliQ water (purified with an NANO pure II system; Barnstead/Thermolyne Corp.; Dubuque, Iowa) for 30 minutes and sterilized with 70% ethanol for 30 seconds followed by 20% Clorox for 20 min on an agitating shaker.

The M0 mutant populations were then screened on tissue culture media containing varying levels of leucine (2-10 mM). Thus, after rinsing with sterile MiliQ water at least 5 times, the seeds (about 50 seeds per plate) were suspended in solidified phytoagar plates with ½ Murashige and Skoog Salt (MSS) medium+1.5% sucrose, 5 g pytoagar and selection agent (leucine). MSS medium is described in Table 1 of U.S. Pat. No. 7,173,170; the description of this medium is incorporated by reference herein in its entirety. The seeds were allowed to germinate in a tissue culture room at 25° C. with a 16-h photoperiod using cool-white fluorescent lamps (Sylvania, Danvers, Mass.) with an intensity of approximately 80 µE $m^{-2}$ $s^{-1}$. After 10 days, the growth medium was removed and the same medium containing leucine at a concentration of 2 to 5 mM, was added to the seedlings. The surviving plants were then transplanted into soil and grown in a greenhouse for development of N. tabacum lines resistant to high levels of leucine.

Surviving M0 plantlets selected on leucine-rich media were rescued and transferred to soil in a growth room. Later, these M0 plants were transferred to the greenhouse and self-seed was collected from each plant and designated as M1. M1 lines were grown under normal field conditions. Each M1 line was flue-cured according to traditional practices.

The EMS mutation breeding lines selected as being able to grow on high amounts of leucine were isolated and characterized. Midribs were removed from each flue-cured leaf sample and were submitted for leaf processing to make cut filler tobacco. Upper and middle stalk leaves were analyzed for amino acids, nicotine, reducing sugars, and total sugars. The results of these analyses are presented in Tables 1-6. Tobacco lines (e.g., 10NH-5, 10NH-18 and 10NH-23) with reduced levels of asparagine as compared to the control are shown in bold font in Table 1. It can be seen that several of the tobacco lines have reductions in other amino acids as well.

TABLE 1

Flue-cured upper stalk leaves (Ala-Gly)

| | Alanine | Arginine | Asparagine | Aspartic Acid | Glutamic Acid | Glutamine | Glycine |
|---|---|---|---|---|---|---|---|
| FC Up 10NH-3 (Sp227) (Control) | 0.633 | <0.137 | 1.158 | 0.113 | 0.147 | 0.896 | 0.061 |
| FC Up 10NH-5 | 0.597 | <0.137 | 0.332 | <0.106 | <0.116 | 0.358 | <0.059 |
| FC Up 10NH-18 | 0.723 | <0.148 | 0.810 | <0.115 | 0.211 | 1.325 | 0.064 |
| FC Up 10NH-23 | 0.498 | <0.129 | 0.442 | <0.1 | <0.11 | 0.433 | <0.056 |
| FC Up 10NH-32 | 0.927 | 0.217 | 5.647 | 0.727 | 0.404 | 1.833 | 0.098 |
| FC Up 10NH-39 | 1.029 | 0.179 | 4.238 | 0.299 | 0.578 | 5.417 | 0.119 |
| FC Up 10NH-34 | 0.628 | <0.144 | 1.706 | 0.182 | 0.247 | 1.515 | 0.088 |
| FC Up 10NH-9 | 0.771 | <0.137 | 2.424 | 0.429 | 0.261 | 1.473 | 0.078 |
| FC Up 10NH-27 | 0.763 | <0.141 | 1.863 | 0.228 | 0.197 | 1.307 | 0.081 |
| FC Up 10NH-47 | 0.896 | <0.14 | 3.719 | 0.421 | 0.304 | 1.773 | 0.061 |

TABLE 2

Flue-cured upper stalk leaves (His-Ser)

| | Histidine | Iso-leucine | Leucine | Lysine | Methionine | Phenyl-alanine | Proline | Serine |
|---|---|---|---|---|---|---|---|---|
| FC Up 10NH-3 (Sp227) (Control) | <0.121 | <0.105 | <0.105 | <0.117 | <0.117 | <0.131 | 7.11 | 0.088 |
| FC Up 10NH-5 | <0.122 | <0.106 | <0.106 | <0.118 | <0.118 | <0.131 | 5.027 | <0.084 |
| FC Up 10NH-18 | 0.135 | <0.114 | <0.114 | <0.128 | <0.128 | <0.142 | 7.715 | 0.122 |
| FC Up 10NH-23 | <0.115 | <0.099 | <0.099 | <0.111 | <0.111 | <0.123 | 5.344 | <0.079 |
| FC Up 10NH-32 | 0.262 | <0.105 | <0.105 | 0.238 | <0.117 | 0.343 | 10.792 | 0.152 |
| FC Up 10NH-39 | 0.352 | <0.108 | <0.108 | 0.304 | <0.12 | 0.22 | 5.215 | 0.303 |
| FC Up 10NH-34 | 0.152 | <0.111 | <0.111 | <0.124 | <0.124 | <0.137 | 6.614 | 0.163 |
| FC Up 10NH-9 | 0.209 | <0.106 | <0.106 | <0.118 | <0.118 | 0.194 | 6.625 | 0.107 |
| FC Up 10NH-27 | 0.175 | <0.109 | <0.109 | <0.121 | <0.121 | <0.135 | 5.583 | <0.087 |
| FC Up 10NH-47 | 0.207 | <0.108 | <0.108 | 0.275 | <0.12 | 0.267 | 6.586 | <0.086 |

TABLE 3

Flue-cured upper stalk leaves (Thr-Val, Total Amino Acids, Nicotine, and Sugars)

| | Threonine | Tyrosine | Valine | Total | Nicotine % | Reducing Sugar % | Total Sugar % |
|---|---|---|---|---|---|---|---|
| FC Up 10NH-3 (Sp227) (Control) | <0.094 | <0.144 | <0.088 | 10.206 | 3.43 | 16 | 20.9 |
| FC Up 10NH-5 | <0.095 | <0.144 | <0.088 | 6.314 | 2.13 | 20.3 | 24.6 |
| FC Up 10NH-18 | <0.103 | <0.156 | <0.095 | 11.105 | 3.78 | 14.9 | 16.5 |
| FC Up 10NH-23 | <0.089 | <0.136 | <0.083 | 6.717 | 2.78 | 17.6 | 23.6 |
| FC Up 10NH-32 | 0.149 | <0.143 | 0.089 | 21.878 | 3.23 | 6.9 | 8.1 |
| FC Up 10NH-39 | 0.176 | <0.147 | 0.125 | 18.554 | 4.18 | 8.8 | 10.2 |
| FC Up 10NH-34 | 0.132 | <0.151 | 0.092 | 11.427 | 3.96 | 12 | 14.2 |
| FC Up 10NH-9 | <0.095 | <0.144 | <0.088 | 12.571 | 3.45 | 11.2 | 16.5 |
| FC Up 10NH-27 | <0.098 | <0.148 | <0.09 | 10.197 | 5.13 | 11.8 | 14.9 |
| FC Up 10NH-47 | <0.097 | <0.147 | <0.09 | 14.448 | 3.78 | 12.4 | 14.1 |

TABLE 4

Flue-cured middle stalk leaves (Ala-Gly)

| | Alanine | Arginine | Asparagine | Aspartic Acid | Glutamic Acid | Glutamine | Glycine |
|---|---|---|---|---|---|---|---|
| FC Mid 10NH-3 (Sp227) (Control) | 0.527 | <0.137 | 0.223 | <0.106 | 0.116 | 0.233 | <0.059 |
| FC Mid 10NH-5 | 0.398 | <0.131 | 0.211 | 0.105 | 0.111 | 0.188 | <0.057 |
| FC Mid 10NH-18 | 0.591 | <0.138 | 1.185 | 0.267 | 0.276 | 1.033 | <0.06 |
| FC Mid 10NH-23 | 0.431 | <0.139 | 0.158 | <0.108 | 0.118 | 0.176 | <0.06 |
| FC Mid 10NH-32 | 0.796 | <0.135 | 3.058 | 0.667 | 0.314 | 1.006 | 0.096 |
| FC Mid 10NH-39 | 0.768 | <0.135 | 1.543 | 0.307 | 0.247 | 1.103 | 0.074 |
| FC Mid 10NH-27 | 0.455 | <0.136 | 0.329 | <0.106 | 0.115 | 0.303 | <0.059 |
| FC Mid 10NH-34 | 0.657 | <0.144 | 0.576 | 0.147 | 0.125 | 0.494 | 0.063 |
| FC Mid 10NH-9 | 0.524 | <0.141 | 0.562 | 0.138 | 0.154 | 0.682 | <0.061 |
| FC Mid 10NH-47 | 0.489 | <0.131 | 0.91 | 0.24 | 0.159 | 0.748 | <0.057 |

TABLE 5

Flue-cured middle stalk leaves (His-Ser)

| | Histidine | Iso-leucine | Leucine | Lysine | Methionine | Phenyl-alanine | Proline | Serine |
|---|---|---|---|---|---|---|---|---|
| FC Mid 10NH-3 (Sp227) (Control) | <0.125 | <0.105 | <0.106 | <0.115 | <0.118 | <0.131 | 4.256 | <0.084 |
| FC Mid 10NH-5 | <0.12 | <0.101 | <0.101 | <0.11 | <0.113 | <0.126 | 2.247 | <0.08 |
| FC Mid 10NH-18 | 0.15 | <0.106 | <0.106 | 0.309 | <0.118 | 0.188 | 6.015 | 0.163 |
| FC Mid 10NH-23 | <0.127 | <0.107 | <0.107 | <0.116 | <0.119 | <0.133 | 3.582 | <0.085 |
| FC Mid 10NH-32 | 0.134 | <0.104 | <0.104 | 0.322 | <0.116 | 0.178 | 7.308 | 0.113 |
| FC Mid 10NH-39 | <0.123 | <0.104 | <0.104 | 0.311 | <0.116 | 0.171 | 4.267 | <0.082 |
| FC Mid 10NH-27 | <0.121 | <0.105 | <0.105 | <0.117 | <0.117 | <0.13 | 4.108 | <0.083 |
| FC Mid 10NH-34 | <0.128 | <0.111 | <0.111 | <0.124 | <0.124 | <0.137 | 4.789 | <0.088 |
| FC Mid 10NH-9 | <0.125 | <0.109 | <0.109 | <0.121 | <0.121 | <0.135 | 4.127 | <0.087 |
| FC Mid 10NH-47 | <0.116 | <0.101 | <0.101 | <0.113 | 0.13 | <0.125 | 4.043 | <0.08 |

TABLE 6

Flue-cured middle stalk leaves (Thr-Val, Total Amino Acids, Nicotine, and Sugars)

| | Threonine | Tyrosine | Valine | Total | Nicotine % | Reducing Sugar % | Total Sugar % |
|---|---|---|---|---|---|---|---|
| FC Mid 10NH-3 (Sp227) (Control) | <0.095 | <0.144 | <0.088 | 5.239 | 2.68 | 20.6 | 25.4 |
| FC Mid 10NH-5 | <0.091 | <0.138 | <0.084 | 3.149 | 1.7 | 24.3 | 34.1 |
| FC Mid 10NH-18 | <0.095 | <0.144 | <0.088 | 10.177 | 3.04 | 13.2 | 16.9 |
| FC Mid 10NH-23 | <0.096 | <0.146 | 0.089 | 4.347 | 2.17 | 23.6 | 30.2 |
| FC Mid 10NH-32 | 0.109 | <0.142 | 0.086 | 14.101 | 2.68 | 10 | 11.4 |
| FC Mid 10NH-39 | <0.093 | <0.141 | 0.086 | 8.791 | 2.37 | 15.6 | 16.6 |
| FC Mid 10NH-27 | <0.094 | <0.143 | 0.087 | 5.195 | 2.61 | 20.1 | 24.5 |
| FC Mid 10NH-34 | <0.099 | <0.151 | <0.092 | 6.851 | 3.04 | 16.3 | 18 |
| FC Mid 10NH-9 | <0.098 | <0.148 | <0.09 | 6.187 | 2.49 | 18.5 | 26.4 |
| FC Mid 10NH-47 | <0.09 | <0.138 | <0.084 | 6.719 | 2.64 | 20.1 | 25.5 |

EXAMPLE 2—Tobacco Having Reduced Asparagine Produces Reduced Acrylamide

Cigarettes for testing were made using a laboratory apparatus as described in US Patent Application Publication No. US 20070006888. Single grade flue-cured tobacco leaf (middle and upper stalk) was used to make the cigarettes and tested for acrylamide and acrylonitrile. Also, a commercial tobacco blend was tested as a control, to determine the precision and accuracy of testing by excising the blend from commercial cigarettes and making cigarettes with this blend.

Three cigarettes were smoked from each tobacco and the smoke was collected using a Cerulean SM 450 smoking machine (Cerulean, Linford Wood East, MK14 6LY, UK). The machine air flows were tuned for ISO conditions (ISO 3308: Routine analytical cigarette smoking machine-definitions and standard conditions; Reference number ISO 3308: 1991 (E) International Organization for Standards, Geneva, Switzerland, 1991; ISO 4387: Cigarette—Determination of total and nicotine free dry particulate matter using a routine analytical smoking machine; Reference number ISO 4387: 1991 (E) International Organization for Standards, Geneva, Switzerland, 1991).

The smoking was performed under one single regimen, using 35 mL puff volume, 2 second puff, and 60 second puff interval (indicated as ISO). The analyses of acrylamide were performed using procedures previously described (S. C. Moldoveanu and A. R. Gerardi, Acrylamide analysis in tobacco, alternative tobacco products, and cigarette smoke, *J. Chromatogr. Sci.*, 49: 234-242, 2011). All analyses were performed in triplicate (including smoking).

The results for the analyses of tobaccos for levels of asparagine, nicotine (Nic), reducing sugars and total sugars are summarized in Tables 7 and 8. Example data is shown in Table 7. It can be seen that several of the lines (e.g., 10NH-5, 10NH-18 and 10NH-23) have significantly reduced levels of asparagine (ASN).

TABLE 7

Level of key compounds in flue-cured upper stalk tobaccos

| Sample | ASN (µg/Mg) in Cured Leaf | % Nic | % Reducing Sugar | % Total Sugar |
|---|---|---|---|---|
| Up-10NH-2 | 1.878 | 3.40 | 13.4 | 18.2 |
| Up-10NH-3 (Control) | 1.158 | 3.43 | 16.0 | 20.9 |
| Up-10NH-5 | 0.332 | 2.13 | 20.3 | 24.6 |
| Up-10NH-9 | 2.424 | 3.45 | 11.2 | 16.5 |
| Up-10NH-18 | 0.810 | 3.78 | 14.9 | 16.5 |
| Up-10NH-23 | 0.442 | 2.78 | 17.6 | 23.6 |
| Up-10NH-27 | 1.863 | 5.13 | 11.8 | 14.9 |
| Up-10NH-32 | 5.647 | 3.23 | 6.90 | 8.1 |
| Up-10NH-34 | 1.706 | 3.96 | 12.0 | 14.2 |
| Up-10NH-39 | 4.238 | 4.18 | 8.8 | 10.2 |
| Up-10NH-47 | 3.719 | 3.78 | 12.4 | 14.1 |

The smoke from three groups of cigarettes was further analyzed for carbon monoxide (CO), total particulate matter (TPM) and acrylamide. One group was a control made with a blend of a commercial tobacco. It was found that the level of precision for the testing procedure was less than 5% relative standard deviation (RSD) (data not shown). The second group (Table 8) included cigarettes made with the upper stalk tobaccos, and the third group (Table 9) included cigarettes made with the middle stalk tobaccos. The analyses were randomized, regarding both the upper or lower stalk samples as well as the replicates of the same sample. The results are given below separately for each group, as averages of three separate analyses. As for the commercial blend, for the analysis of TPM and for acrylamide, the replicates showed less than 5% relative standard deviations (RSD %).

TABLE 8

Smoke analysis results, including acrylamide levels in flue-cured upper stalk tobaccos

| Sample | Puff No./cig | CO mg/cig | TPM mg/cig | Acrylamide µg/cig | Acryl./TPM µg/mg | T-test |
|---|---|---|---|---|---|---|
| Up-10NH-2 K326 Conrol | 10.56 | 9.47 | 15.02 | 1.20 | 0.080 | G |
| Up-10NH-3 Sp227 Control | 10.11 | 11.00 | 16.63 | 1.11 | 0.067 | G |
| Up-10NH-5 | 10.42 | 11.23 | 16.29 | 0.64 | 0.040 | H |
| Up-10NH-9 | 9.79 | 10.56 | 17.67 | 1.70 | 0.096 | D |
| Up-10NH-18 | 10.89 | 9.71 | 15.68 | 0.70 | 0.045 | H |
| Up-10NH-23 | 10.32 | 12.35 | 17.86 | 0.67 | 0.038 | H |
| Up-10NH-27 | 11.00 | 11.21 | 17.71 | 1.48 | 0.084 | E |
| Up-10NH-32 | 9.09 | 8.54 | 15.02 | 3.32 | 0.221 | A |
| Up-10NH-34 | 10.34 | 10.12 | 16.83 | 1.30 | 0.078 | F |
| Up-10NH-39 | 11.12 | 9.95 | 16.47 | 2.69 | 0.163 | B |
| Up-10NH-47 | 10.02 | 9.79 | 17.17 | 2.11 | 0.123 | C |

Tobaccos having a level of acrylamide/TPM with reduced ratio compared to the control (e.g., 10NH-5, 10NH-18, and 10NH-23) are shown in bold font.

TABLE 9

Smoke analysis results, including acrylamide levels in flue-cured middle stalk tobaccos

| Sample | Puff No./cig | CO mg/cig | TPM mg/cig | Acrylamide µg/cig | Acryl./TPM µg/mg |
|---|---|---|---|---|---|
| Md-10NH-3 Control | 9.80 | 10.65 | 12.92 | 0.37 | 0.029 |
| Md-10NH-5 | 9.49 | 11.26 | 12.17 | 0.30 | 0.025 |
| Md-10NH-9 | 9.68 | 9.00 | 11.41 | 0.42 | 0.037 |
| Md-10NH-18 | 8.33 | 7.12 | 9.33 | 0.52 | 0.056 |
| Md-10NH-23 | 9.96 | 9.79 | 12.18 | 0.74 | 0.061 |
| Md-10NH-27 | 9.57 | 8.52 | 12.49 | 1.29 | 0.103 |
| Md-10NH-32 | 9.53 | 9.36 | 12.89 | 0.42 | 0.033 |
| Md-10NH-39 | 10.27 | 9.38 | 12.57 | 0.67 | 0.053 |
| Md-10NH-34 | 9.30 | 11.15 | 14.29 | 0.50 | 0.035 |
| Md-10NH-47 | 9.63 | 9.58 | 13.07 | 0.71 | 0.054 |

The results from Tables 8 and 9 indicate that various EMS modified tobaccos lead to the formation of a range of acrylamide levels in cigarette smoke. Several EMS tobacco lines (10NH-5, 10NH-18, and 10NH-23) had a lower level of acrylamide in smoke as found in three upper stalk tobaccos and one middle stalk tobacco (data not shown).

The data from the upper stalk samples was analyzed using a one-way student's T-test. It was found that each of the plants were significantly different from the control (Table 8). As shown in Table 8, samples represented by a different letter (e.g., A, B, C etc) had statistically significant different values of the mean for acrylamide.

Figure 2:
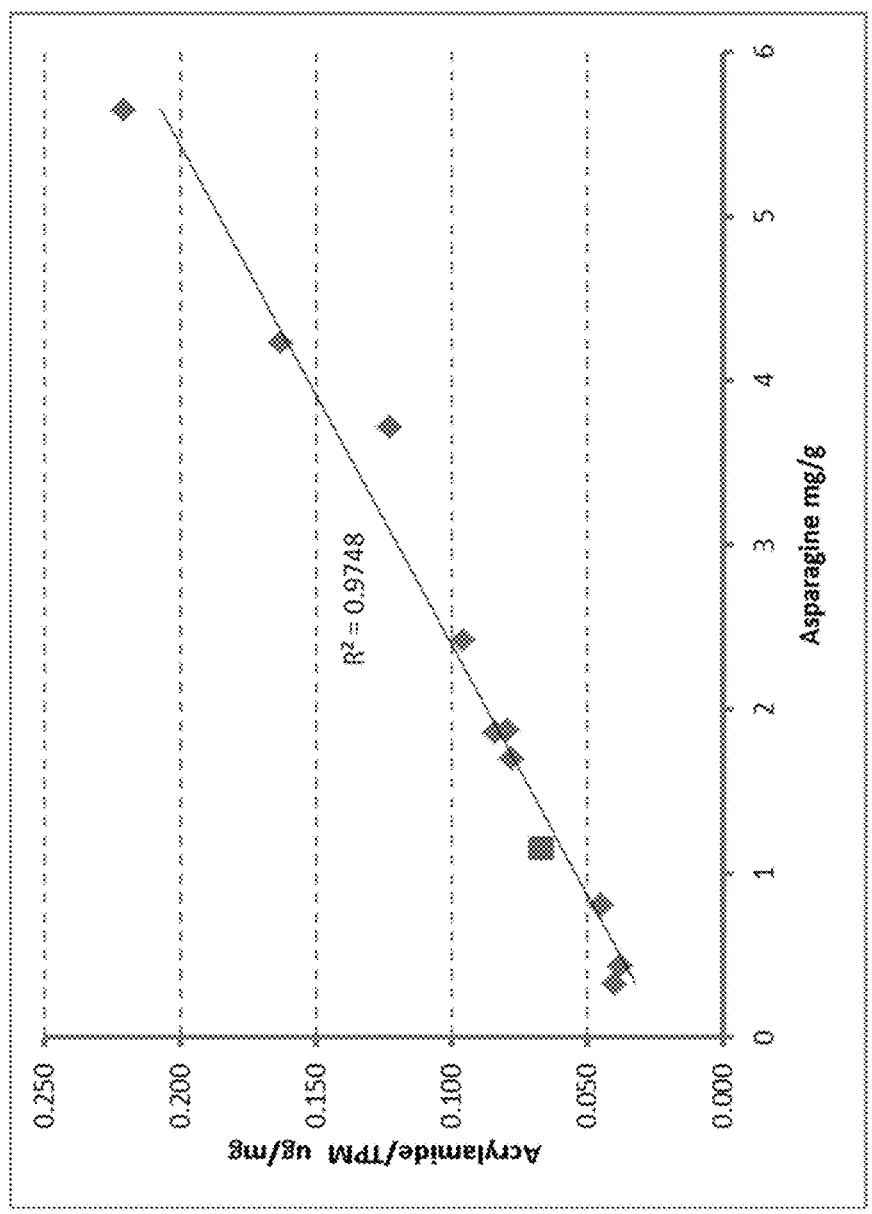
FIG. 2 shows a correlation between the level of asparagine measured as milligrams (mg) per gram tobacco and the level of acrylamide measured as micrograms (μg) per total particulate matter (TPM) of tobacco according to one embodiment of the invention. The control strain (10NH-3) is shown as a square; values for the various experimental strains are shown as diamond shaped symbols.

This results indicate that reduction of acrylamide in cigarette smoke can be achieved using the mutagenic modification of the plant. FIG. 2 illustrates that the increase or decrease of acrylamide level was achieved by the modification of amino acid content in the plant. Thus, there was an excellent correlation between the asparagine level and acrylamide in smoke can be seen for upper stalk tobaccos. The control strain (10NH-3) is shown as a square; values for the various experimental strains are shown as diamond shaped symbols.

EXAMPLE 3—Tobacco Having Reduced Acrylonitrile

Tables 10 and 11 provide results for acrylonitrile (ANI) levels from cigarettes made with the upper stalk tobaccos (Table 10), and cigarettes made with the middle stalk tobaccos (Table 11). Acrylonitrile was measured according to previously published procedures (S. C. Moldoveanu, 2010, Beitr. Tabakforsch. Int., 24:145-156). Again, the analyses were randomized, regarding both the upper or lower stalk samples as well as the replicates of the same sample. The results are given below separately for each group, as averages of three separate analyses. As for the commercial blend, for the analysis of TPM and for acrylonitrile, the replicates showed less than 5% relative standard deviations (RSD %). The results for cigarette puff number, CO, TPM, and acrylonitrile for the upper stalk cigarettes made with EMS mutagenized tobaccos are shown in Table 10 and those for middle stalk are shown in Table 11.

TABLE 10

Smoke analysis results, including acrylonitrile levels in flue-cured upper stalk tobaccos

| Sample | Puff No./cig | CO mg/cig | TPM mg/cig | Acrylo-nitrile µg/cig | ANI/TPM µg/mg | T-test |
|---|---|---|---|---|---|---|
| Up-10NH-3 Sp 227 Control | 10.11 | 11.00 | 16.63 | 5.18 | 0.311 | A |
| *Up-10NH-5* | *10.42* | *11.23* | *16.29* | *2.65* | *0.163* | *G* |
| *Up-10NH-18* | *10.89* | *9.71* | *15.68* | *2.61* | *0.166* | *G* |
| *Up-10NH-23* | *10.32* | *12.35* | *17.86* | *3.42* | *0.191* | *C* |
| Up-10NH-32 | 9.09 | 8.54 | 15.02 | 4.38 | 0.292 | B |
| Up-10NH-39 | 11.12 | 9.95 | 16.47 | 4.27 | 0.259 | B |
| Up-10NH-34 | 10.34 | 10.12 | 16.83 | 2.83 | 0.168 | F |
| Up-10NH-9 | 9.79 | 10.56 | 17.67 | 2.99 | 0.169 | E |
| Up-10NH-27 | 11.00 | 11.21 | 17.71 | 2.59 | 0.146 | G |
| Up-10NH-47 | 10.02 | 9.79 | 17.17 | 3.22 | 0.188 | D |
| Minimum | | | | | 0.146 | |

TABLE 11

Smoke analysis results, including acrylonitrile levels in flue-cured middle stalk tobaccos

| Sample | Puff No./cig | CO mg/cig | TPM mg/cig | Acrylonitrile µg/cig | ANI/TPM µg/mg |
|---|---|---|---|---|---|
| Mid-10NH-3 Control | 9.80 | 10.65 | 12.92 | 5.48 | 0.424 |
| Mid-10NH-5 | 9.49 | 11.26 | 12.17 | 4.47 | 0.367 |
| Mid-10NH-18 | 8.33 | 7.12 | 9.33 | 4.07 | 0.436 |
| Mid-10NH-23 | 9.96 | 9.79 | 12.18 | 4.28 | 0.351 |
| Mid-10NH-32 | 9.53 | 9.36 | 12.89 | 4.64 | 0.360 |
| Mid-10NH-39 | 10.27 | 9.38 | 12.57 | 4.30 | 0.342 |
| Mid-10NH-27 | 9.57 | 8.52 | 12.49 | 4.07 | 0.326 |
| Mid-10NH-34 | 9.30 | 11.15 | 14.29 | 3.60 | 0.252 |
| Mid-10NH-9 | 9.68 | 9.00 | 11.41 | 3.80 | 0.333 |
| Mid-10NH-47 | 9.63 | 9.58 | 13.07 | 3.82 | 0.292 |
| Minimum | | | | | 0.252 |

It can be seen that as compared to the control, for the upper stalk leaves the lowest acrylonitrile level generated from one of the EMS-mutagenized plants was only 47% from that of the parent, and for the middle stalk leaves the lowest acrylonitrile level was only 59% of the parent. The data from the upper stalk samples was analyzed using a one-way student's T-test. It was found that each of the plants were significantly different from the control (Table 10). As shown in Table 10, samples represented by a different letter (e.g., A, B, C etc) had statistically significant different values of the mean for acrylonitrile. The three lines showing reduced acrylonitrile and reduced acrylamide (10NH-5, 10-NH-18, and 10NH-23) are shown in italics in Table 10. Also, lines 10NH-27, 10NH-34 and 10NH-9 exhibited low acrylonitrile levels.

Further work was performed to attempt the identification of a major amino acid precursor for the generation of acrylonitrile. The correlation coefficients R between the amino acid level given in Tables 1-3 in the upper stalk leaf in mg/g tobacco and acrylonitrile/TPM (µg/mg) are shown in Table 12. The same results for the middle stalk tobaccos with the analytical results given Tables 4-6 in are shown in Table 13. Some of the results for the amino acids were reported as "lower than" based on the limit of quantitation (LOQ) of the analytical method. Since the correlation calculations required a number, this LOQ value was used for the amino acids where a true level was not known.

TABLE 12

Correlation coefficients R between the amino acid level in the upper stalk tobaccos in mg/g and acrylonitrile/TPM (µg/mg)

| Alanine | Arginine | Asparagine | Aspartic Acid | Glutamic Acid | Glutamine | Glycine | Histidine | Isoleucine |
|---|---|---|---|---|---|---|---|---|
| 0.332174 | 0.578436 | 0.483586 | 0.341411 | 0.404984 | 0.333144 | 0.323972 | 0.371866 | −0.32616 |

| Leucine | Lysine | Methionine | Phenyl-alanine | Proline | Serine | Threonine | Tyrosine | Valine |
|---|---|---|---|---|---|---|---|---|
| −0.32616 | 0.415565 | −0.33681 | 0.445296 | 0.485969 | 0.346656 | 0.45159 | −0.29462 | 0.251272 |

| Total | Nicotine % | Reducing Sugar % | Total Sugar % | CO mg/cig | TPM mg/cig | ANI µg/cig | ANI/TPM |
|---|---|---|---|---|---|---|---|
| 0.549845 | −0.12322 | −0.32378 | −0.28585 | −0.3344 | −0.47169 | 0.980999 | 1 |

TABLE 13

Correlation coefficients R between the amino acid levels in the middle stalk tobaccos in mg/g and acrylonitrile/TPM (μg/mg)

| Alanine | Arginine | Asparagine | Aspartic Acid | Glutamic Acid | Glutamine | Glycine | Histidine | Isoleucine |
|---|---|---|---|---|---|---|---|---|
| −0.06259 | −0.20168 | 0.063787 | 0.08524 | 0.306823 | 0.055229 | 0.013527 | 0.539314 | −0.25738 |

| Leucine | Lysine | Methionine | Phenyl-alanine | Proline | Serine | Threonine | Tyrosine | Valine |
|---|---|---|---|---|---|---|---|---|
| −0.20865 | 0.363996 | −0.57727 | 0.418078 | 0.170998 | 0.548165 | −0.0102 | −0.24009 | −0.2004 |

| Total | Nicotine % | Reducing Sugar % | Total Sugar % | CO mg/cig | TPM mg/cig | ANI μg/cig | ANI/TPM |
|---|---|---|---|---|---|---|---|
| 0.138001 | −0.07323 | −0.07871 | 0.011481 | −0.35976 | −0.68422 | 0.691697 | 1 |

As seen from Tables 12 and 13, the correlation coefficients for the upper stalk tobaccos and for the middle stalk tobaccos show higher R values for glutamic acid, histidine, lysine, phenylalanine and serine. Glutamic acid has been proven to be a contributor to the formation of acrylonitrile.

Thus, the methods of the present invention utilize a rapid and economical mutagenesis method for developing plant lines having decreased levels of at least one amino acid. In an embodiment, the plant is tobacco. The invention provides a method whereby mutagenized tobacco seeds are allowed to germinate under selective conditions, and then chimeric plants at least partially comprising a phenotype resistant to high concentrations of leucine are selected. Included in the present invention are modified tobacco lines having a decrease in asparagine and/or glutamic acid. Such tobaccos form reduced amounts of the potential carcinogen acrylamide or acrylonitrile, respectively, upon heating and/or burning. These genetically modified tobacco lines can be used as germplasm to develop new tobacco varieties with altered amino acid profiles and/or can be mixed with other strains of tobacco to produce a blend having improved taste and aroma.

All references cited herein are incorporated by reference in their entirety.

What is claimed is:

1. A method for producing a modified tobacco plant comprising generating a tobacco plant comprising a reduced level of asparagine, such that the tobacco plant or a portion thereof generates a reduced level of acrylonitrile upon heating or burning as compared to an unmodified parent tobacco plant or a portion thereof, wherein the producing comprises the steps of exposing a tobacco seed from the unmodified tobacco plant to a mutagen and then growing a seedling generated from the seed in the presence of leucine as a selection agent.

2. The method of claim 1, wherein the modified tobacco plant further comprises reduced levels of glutamic acid.

3. The method of claim 1 comprising the steps of:
incubating the at least one tobacco seed from an unmodified tobacco plant in a solution comprising a mutagen;
washing the at least one seed free of the mutagen;
exposing the at least one seed to the leucine selection agent;
germinating the at least one seed and growing at least one M0 tobacco seedling in the presence of the selection agent;
growing the at least one M0 tobacco seedling to generate at least one M0 tobacco plant comprising at least one mutagenized M1 tobacco seed; and
germinating the at least one mutagenized M1 tobacco seed to select for at least one modified M1 tobacco plant comprising a reduced level of asparagine as compared to the unmodified tobacco plant.

4. The method of claim 1, wherein the reduction in acrylonitrile is at least 10%.

5. The method of claim 1, wherein the reduction in acrylonitrile is at least 20%.

6. The method of claim 1, wherein the reduction in acrylonitrile is at least 30%.

7. The method of claim 1, wherein the reduction in acrylonitrile is at least 40%.

8. The method of claim 1, wherein the modified tobacco plant is the species *Nicotiana tabacum*.

9. The method of claim 3, further comprising the steps of:
growing at least one of the M1 tobacco plants to generate M2 tobacco seeds, wherein the least one M1 tobacco plant is a homozygote for a mutation conferring the ability to grow in the presence of the leucine selection agent.

10. The method of claim 1, wherein the modified tobacco plant comprises at least one of the 10NH-18, 10NH-23, 10NH-27, 10NH-34 or 10NH-9 lines, representative seeds of which have been deposited under ATCC Accession Nos. PTA-12341, PTA-12339, PTA-12342, PTA-12340, and PTA-12343, respectively.

11. A modified tobacco plant or a portion thereof comprising a decrease in the level of acrylonitrile upon heating and/or burning as compared to an unmodified tobacco from which the plant is derived and comprising at least one of the 10NH-18, 10NH-23, 10NH-27, 10NH-34 or 10NH-9 lines, representative seeds of which have been deposited under ATCC Accession Nos. PTA-12341, PTA-12339, PTA-12342, PTA-12340, and PTA-12343, respectively.

12. The modified tobacco plant of claim 11, wherein the reduction in acrylonitrile is at least 10%.

13. The modified tobacco plant of claim 11, wherein the reduction in acrylonitrile is at least 20%.

14. The modified tobacco plant of claim 11, wherein the reduction in acrylonitrile is at least 30%.

15. A tobacco product comprising a modified tobacco from the modified tobacco plant or the portion thereof of claim 11.

16. The tobacco product of claim 15, comprising tobacco from at least one of the 10NH-18 or 10NH-23 lines, representative seeds of which have been deposited under ATCC Accession Nos. PTA-12341 and PTA-12339, respectively, wherein the tobacco comprises a reduction in asparagine and/or glutamic acid levels.

17. The tobacco product of claim 15, wherein the reduction in acrylonitrile is at least 10%.

18. The tobacco product of claim 15, wherein the reduction in acrylonitrile is at least 20%.

19. The tobacco product of claim 15, wherein the reduction in acrylonitrile is at least 30%.

20. The tobacco plant of claim 11, comprising at least one of the 10NH-18 or 10NH-23 lines, representative seeds of which have been deposited under ATCC Accession Nos. PTA-12341 and PTA-12339, respectively, wherein the tobacco comprises a reduction in-asparagine and/or glutamic acid levels as compared to an unmodified tobacco from which the plant is derived.

* * * * *